United States Patent
Madsen et al.

(10) Patent No.: US 6,318,146 B1
(45) Date of Patent: Nov. 20, 2001

(54) MULTI-IMAGING MODALITY TISSUE MIMICKING MATERIALS FOR IMAGING PHANTOMS

(75) Inventors: Ernest L. Madsen; Warren D. D'Souza; Gary R. Frank, all of Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/353,752

(22) Filed: Jul. 14, 1999

(51) Int. Cl.[7] .................................................. G01N 29/00
(52) U.S. Cl. .............................. 73/1.86; 73/866.4; 436/8; 324/308
(58) Field of Search ................................ 73/1.86, 866.21, 73/1.82; 436/8; 324/308, 309

(56) References Cited

U.S. PATENT DOCUMENTS

| | | | |
|---|---|---|---|
| 4,116,040 | 9/1978 | Skoknecht et al. | 73/1.83 |
| 4,277,367 | 7/1981 | Madsen et al. | 436/8 |

(List continued on next page.)

OTHER PUBLICATIONS

Goldstein, et al., "Particle Image–Resolution Test Object," J. Ultrasound Med. Phys., vol. 2, May (1983), pp. 195–209.

Smith, S.W. and H. Lopez, "A Contrast–Detail Analysis of Diagnostic Ultrasound Imaging," Med. Phys., vol. 9, No. 1, pp. 4–12, Jan./Feb. 1982.

Translation of German patent application publication No. 2814336.

Carson, Paul L., "What a Hospital Physicist Needs in a Transducer Characterization Standard: Are Tissue Equivalent Test Objects Necessary?" IEEE Transactions on Sonics and Ultrasonics, vol. S U–26, No. 1, Jan. 1979, pp. 1–6.

Smith, et al., "Frequency Independent Ultrasound Contrast–Detail Analysis," Ultrasound in Med. & Biol., vol. 11, No. 3, pp. 467–477, May/Jun. 1985.

New Product Announcement, The Wisconsin Spherical Void Phantom, Oct. 1988.

Madsen, et al., "Liquid or Solid Ultrasonically Tissue–Mimicking Materials with Very Low Scatter," Ultrasound in Med. & Biol., vol. 24, No. 4, May, 1998, pp. 535–542.

*Primary Examiner*—Helen Kwok
*Assistant Examiner*—Charles D. Gerber
(74) *Attorney, Agent, or Firm*—Foley & Lardner

(57) ABSTRACT

Tissue-mimicking material suitable for phantoms for use with at least ultrasound and MRI have sections of material in contact with each other which mimic ultrasound and magnetic resonance imaging properties of human tissues, and preferably also computed tomography properties, so that the phantom can be used for the testing of imaging by various types of medical imagers. A suitable tissue-mimicking material for use in phantoms of this type includes an aqueous mixture of large organic water soluble molecules, a copper salt, a chelating agent for binding the copper ions in the salt, and a gel-forming material. Small glass beads may be intermixed therewith to provide a selected ultrasound attenuation coefficient without substantially affecting the MRI properties of the material. Larger glass beads may be used in a section to control primarily the ultrasound backscatter coefficient without significant effect on the ultrasound attenuation coefficient. Tissue-mimicking material that simulates muscle may have smaller glass beads and a higher concentration of gel-forming material than an adjacent section. Such similar materials in contact with one another show relative stability over extended periods of time.

43 Claims, 14 Drawing Sheets

U.S. PATENT DOCUMENTS

| | | | |
|---|---|---|---|
| 4,286,455 | | 9/1981 | Ophir et al. .................... 73/1.83 |
| 4,331,021 | | 5/1982 | Lopez et al. .................... 73/1.86 |
| 4,406,153 | | 9/1983 | Ophir et al. .................... 73/1.86 |
| 4,417,582 | | 11/1983 | Trimmer et al. ................ 600/437 |
| 4,453,408 | | 6/1984 | Clayman ........................ 73/1.86 |
| 4,470,303 | * | 9/1984 | O'Donnell ...................... 73/602 |
| 4,542,745 | * | 9/1985 | Oakley et al. .................. 252/312 |
| 4,644,276 | * | 2/1987 | Sierocuk et al. ................ 324/307 |
| 4,729,892 | * | 3/1988 | Beall ............................. 424/9 |
| 4,843,866 | | 7/1989 | Madsen et al. ................. 73/1.86 |
| 5,054,310 | | 10/1991 | Flynn ............................ 73/1.86 |
| 5,164,978 | * | 11/1992 | Goodenough et al. ......... 378/207 |
| 5,196,343 | * | 3/1993 | Zerhouni et al. ............... 436/8 |
| 5,289,831 | * | 3/1994 | Bosley .......................... 128/899 |
| 5,312,755 | | 5/1994 | Madsen et al. ................. 436/8 |
| 5,336,999 | * | 8/1994 | Mansfield et al. ............. 324/309 |
| 5,542,935 | * | 8/1996 | Unger et al. .................... 604/190 |
| 5,574,212 | | 11/1996 | Madsen et al. ................. 73/1.86 |
| 5,625,137 | | 4/1997 | Madsen et al. ................. 73/1.84 |
| 5,670,719 | | 9/1997 | Madsen et al. ................. 73/619 |
| 5,756,875 | * | 5/1998 | Parker et al. ................... 73/1 DV |
| 5,827,942 | | 10/1998 | Madsen et al. ................. 73/1.82 |
| 5,886,245 | * | 3/1999 | Flax .............................. 73/1.86 |
| 5,902,748 | * | 5/1999 | Madsen et al. ................. 436/8 |
| 5,922,304 | * | 7/1999 | Unger ............................ 424/9.3 |
| 5,951,475 | * | 9/1999 | Gueziec et al. ................ 600/425 |
| 6,008,644 | * | 12/1999 | Leunbach et al. .............. 324/300 |
| 6,011,626 | * | 1/2000 | Hielscher et al. .............. 356/367 |
| 6,148,655 | * | 11/2000 | Hall et al. ...................... 73/1.86 |
| 6,190,915 | * | 2/2001 | Madsen et al. ................. 436/8 |
| 6,205,871 | * | 3/2001 | Saloner et al. ................. 73/866.4 |

* cited by examiner

MULTI-IMAGING MODALITY TISSUE MIMICKING MATERIALS FOR IMAGING PHANTOMS

FIELD OF THE INVENTION

This invention pertains generally to the field of phantoms for use with medical imaging such as ultrasound scanning, magnetic resonance imaging and computed tomography.

BACKGROUND OF THE INVENTION

There has been a tremendous surge in the number of ultrasound guided transperineal prostate implants performed in recent years. Effective implants require involved treatment planning based on three-dimensional multi-modality (magnetic resonance imaging, ultrasound, computed tomography) images used in combination with one another. A multi-modality prostate imaging phantom could have applications in quality assurance, image registration and treatment planning. Three human soft tissues relevant to a prostate phantom that should be mimicked for magnetic resonance imaging (MRI), ultrasound, and computed tomography (CT) are prostate parenchyma, skeletal muscle and adipose (fat) tissue.

Tissue-mimicking (TM) materials must exhibit the same properties relevant to a particular imaging modality as actual human soft tissues. Tissue-mimicking materials for use in magnetic resonance imaging phantoms should have values of characteristic relaxation times, T1 and T2, which correspond to those of the tissue represented at the Larmor frequency of concern. Soft tissues exhibit T1 values ranging from about 200–1200 ms and T2 values from about 40–200 ms. For given soft tissue, T1 in particular can exhibit a significant dependence on frequency as well as on temperature. However, for multi-modality imaging phantoms, in general, measurements may be performed near the available clinical Larmor frequency of an MRI system (typically 64 MHz or 85 MHz) and at room temperature. Phantoms must be assumed to be useful at room temperature even though their properties must mimic those of soft tissues at the normal body temperature of 37° C.

The ideal tissue-mimicking material for use in ultrasound should have the same ranges of speeds of sound, attenuation coefficients, and backscatter coefficients as soft tissue. These parameters should be controllable in the manufacturing process of the phantom material, and their variation within the range of room temperatures should be small. Speeds of sound in human soft tissues vary over a fairly small range with an average value of about 1540 m/s. The speed of sound in fat is thought to be about 1470 m/s. The amplitude attenuation coefficients appear to vary over the range from 0.4 dB/cm to about 2 dB/cm at a frequency of 1 MHz in these tissues. The frequency dependencies of the attenuation coefficient of some soft tissues have been studied and, typically, it has been reported that the attenuation coefficient is approximately proportional to the ultrasonic frequency in the diagnostic frequency range of 1 to 10 MHz. An exception is breast fat, in which the attenuation coefficient is proportional to the frequency to the 1.7 power.

F. T. D'Astous and F. S. Foster, "Frequency Dependence of Attenuation and Backscatter in Breast Tissue," Ultrasound in Med. & Biol., Vol. 12, pp. 795–808 (1986).

For use in computed tomography (CT), the tissue-mimicking materials must exhibit the same CT number as that of the tissue being mimicked. The CT numbers for most soft tissues lie in the range of about 20–70 at the typical effective x-ray energy of a clinical CT scanner except for fat where the CT number is about −100.

In addition to the individual imaging modality parameters listed above, tissue-mimicking materials must also exhibit long term stability and ease of storage without which they are rendered useless in an imaging phantom.

An ultrasound phantom containing tissue-mimicking material is disclosed in U.S. Pat. No. 4,277,367, to Madsen, et al., entitled Phantom Material and Methods, in which both the speed of sound and the ultrasonic attenuation properties could be simultaneously controlled in a mimicking material based on water based gels, such as those derived from animal hides. In one embodiment, ultrasound phantoms embodying the desired features for mimicking soft tissue were prepared from a mixture of gelatin, water, n-propanol and graphite powder, with a preservative. In another embodiment, an oil and gelatin mixture formed the basis of the tissue-mimicking material.

Tissue-mimicking material is typically used to form the body of an ultrasound scanner phantom. This is accomplished by enclosing the material in a container which is closed by an ultrasound transmitting window cover. The tissue-mimicking material is admitted to the container in such a way as to exclude air bubbles from forming in the container. Tissue-mimicking materials may contain scattering particles, spaced sufficiently close to each other that an ultrasound scanner is incapable of resolving individual scattering particles. Testing spheres of tissue-mimicking material, or other targets, may be located within the phantom container, suspended in the tissue-mimicking material body. The objective is for the ultrasound scanner to resolve the testing spheres or other targets from the background material and scattering particles. This type of ultrasound phantom is described in U.S. Pat. No. 4,843,866, to Madsen, et al., entitled Ultrasound Phantom.

U.S. Pat. No. 5,625,137 to Madsen, et al. discloses a tissue-mimicking material for ultrasound phantoms with very low acoustic backscatter coefficient that may be in liquid or solid form. A component in both the liquid and solid forms is a filtered aqueous mixture of large organic water soluble molecules and an emulsion of fatty acid esters, which may be based on a combination of milk and water. Hydroxy compounds, such as n-propanol, can be used to control the ultrasonic speed of propagation through the material and a preservative from bacterial invasion can also be included. The use of scattering particles allows a very broad range of relative backscatter levels to be achieved.

Hydrogen magnetic resonance imaging (MRI) (also known as nuclear magnetic resonance, or NMR, imaging) is generally a more complicated imaging procedure than X-ray or ultrasound since it does not measure just one dominant property, such as electron density in the case of X-ray computed tomography, but is affected by the hydrogen atom density, flow, and two relaxation phenomena. The contrast, or differences in image brightness, in an MRI image is primarily due to differences in the relaxation times of tissues. It has been found that there are relaxation time differences between normal tissue and certain tumors, which makes MRI imaging potentially very valuable in early detection of such tumors.

A satisfactory MRI phantom must satisfy several requirements. First, the material of which the phantom is made should mimic the hydrogen density and relaxation times of several types of tissues. Second, the relaxation times of the material should not change over time, such as over several months or years, so that the phantom can be used in tests of imager reproducibility. Third, if the phantom includes inclusions of materials within the surrounding matrix which have different NMR characteristics than the surrounding matrix, these inclusions must be stable over time in both shape and in NMR relaxation times, T1 and T2.

Soft tissues exhibit T2's from about 40 ms to 200 ms. Typical values for the ratio T1/T2 lie between 4 and 10 for soft tissues. For a given soft tissue parenchyma, T1 in particular can exhibit a significant dependence on frequency as well as temperature.

Materials which have been proposed for use in phantoms to mimic soft tissues with respect to one or more NMR properties include aqueous solutions of paramagnetic salts and water based gels of various forms. Such gels may also contain additives such as a paramagnetic salt for control of T1. Aqueous solutions of paramagnetic salts can be used in phantoms to produce a desired value of either T1 or T2. The ratio of T1/T2 in the salt solutions is almost always less than 2, however, rendering such solutions inadequate for the close mimicking of soft tissue, with the possible exception of body fluids.

Phantom materials composed of water based agar gels doped with $MnCl_2$ to control T1 have been reported. R. Mathur-DeVre, et al., "The Use of Agar as a Basic Reference for Calibrating Relaxation Times and Imaging Parameters," Magn. Reson. Med., Vol. 2, 1985, p. 176. Agar gels doped with $CuSO_4$ have also been reported. M. D. Mitchell, et al., "Agarose as a Tissue-Equivalent Phantom Material for NMR Imaging," Magn. Reson. Imag., Vol. 4, 1986, p. 263.

A phantom material consisting of mixtures of agar gel and animal hide gel in which $CuSO_4$ was used to lower T1 has also been reported. Unfortunately, a long-term instability manifested itself in that a steady, very slow rise in T1 was observed over a period of months. This instability precludes the use of this material in MRI phantoms. The rise in $T_1$ was perhaps due to the slow formation of metal-organic complexes, removing the $Cu^{++}$ paramagnetic ions. J. C. Blechinger, et al., "NMR Properties for Tissue-Like Gel Mixtures for Use as Reference Standards or in Phantoms," Med. Phys., Vol. 12, 1985, p. 516 (Abstract).

More recently, the problem of gradual increase in T1 in the agar, animal hide gel, $Cu^{++}SO_4^-$ gel has been eliminated by addition of the chelating agent EDTA (ethylenediaminetetraacetic acid). This stable material is excellent for use in MRI phantoms. See J. R. Rice, et al., "Anthropomorphic $^1H$ MRS Head Phantom," Medical Physics, Vol. 25, 1998, pp. 1145–1156.

U.S. Pat. No. 5,312,755 to Madsen et al. discloses a tissue-mimicking NMR phantom that utilizes a base tissue-mimicking material which is a gel solidified from a mixture of animal hide gelatin, agar, water and glycerol. The amount of glycerol could be used to control the T1. The preferred base material included a mixture of agar, animal hide gelatin, distilled water (preferably deionized), glycerol, n-propyl alcohol, formaldehyde, and p-methylbenzoic acid. The contrast resolution phantom could include inclusions which have NMR properties which differ from the base tissue-mimicking material. Differences in contrast between the surrounding base material and the spherical inclusions could also be obtained by the use of a solid such as powdered nylon added to the base material and the inclusions that has little NMR response but displaces some of the gelatin solution, decreasing the apparent $^1H$ density to the NMR instrument.

As noted above, phantoms for use in MRI systems made from water-based agarose gels along with a copper salt have been made previously. M. D. Mitchell, et al., supra. The T1 and T2 relaxation rates are strongly dependent on the concentrations of agarose and copper ions in the tissue-mimicking sample with the T1 depending more on the copper and the T2 depending more strongly on the concentration of dry weight agarose in the sample. Burlew et al. "A New Ultrasound Tissue-Equivalent Material," Radiology, Vol. 134, 1980, pp. 517–520, have described a polysaccharide gel (agar) for ultrasound phantoms that can be made to exhibit speeds of sound over the range of 1498 m/s to 1600 m/s at 22° C.

A prostate phantom based on CT slices and made from solid water (Gammex/RMI, Madison, Wis.) for imaging, volume rendering, treatment planning, and dosimetry applications has also been constructed. B. B. Paliwal, et al., "A Solid Water Pelvic and Prostate Phantom for Imaging, Volume Rendering, Treatment Planning, and Dosimetry for an RTOG Multi-Institutional, 3-D Dose Escalation Study," International Journal of Radiation Oncology, Biology, Physics, Vol. 42, 1998, pp. 205–211.

An earlier investigation had reported on whether tissue-mimicking (TM) materials for ultrasound might be appropriate for use in magnetic resonance imaging (MRI) phantoms as well. See, E. L. Madsen, et al., "Prospective Tissue-mimicking Material For Use In NMR Imaging Phantoms," Magn. Reson. Imaging, Vol. 1, 1982, pp. 135–141. These materials consisted of powdered graphite and preservatives in water-based proteinaceous gels. Though the materials looked promising initially, later measurements revealed that, although T1 was mimicked adequately, it was the T2* which was being controlled through concentration of graphite, not T2 itself. For tissue-mimicking materials, it is the T2 which must be controlled because T2 is intrinsic to the material whereas T2* is influenced by the involved imager instrumentation.

SUMMARY OF THE INVENTION

In accordance with the invention, a tissue-mimicking material is provided for imaging phantoms that can be used with two or more types of imaging modalities, such as ultrasound scanning, magnetic resonance imaging, and computed tomography. The tissue-mimicking material may be adjusted to appropriately mimic human tissue in the several modes of imaging for particular tissues such as organs, skeletal muscle, and fat. The materials mimicking the various tissues may be incorporated in direct contact with one another in an imaging phantom and remain stable in their multi-modal imaging properties over time, allowing such phantoms to be used for long-term calibration and evaluation of the imaging instruments. Phantoms in accordance with the invention have particular application in simulating prostate tissue which is surrounded by and adjacent to muscle and fat tissue.

Each component material in a tissue-mimicking material influences ultrasound, CT and MRI properties to a greater or lesser extent. There is at least one combination that yields good representation of the essential properties for all three modalities for that tissue-mimicking material (e.g., prostate parenchyma). In addition, different tissue-mimicking materials should be capable of remaining in direct contact without changes in their ultrasound, CT and MRI properties for long periods of time—months or years—to allow construction of anthropomorphic phantoms without the need for unrealistic image-degrading diffusion barrier between tissue-mimicking materials.

A preferred multi-imaging modality tissue-mimicking material for use in phantoms with at least ultrasound and MRI comprises an aqueous mixture of large organic water soluble molecules, a copper salt, a chelating agent for binding the copper ions in the salt, a gel-forming material, and glass or plastic beads intermixed therewith to provide a selected ultrasound attenuation coefficient, the glass or plastic beads selected and treated to have a low effect on the MRI T1 and T2 properties of the tissue-mimicking material. Such a material is particularly suitable for mimicking skeletal muscle tissue in both MRI and ultrasound imaging. A preferred gel-forming material is agarose, a preferred copper salt is $CuCl_2$, and the large organic water soluble molecules are preferable derived from condensed milk. EDTA may be utilized as the chelating agent. The glass beads are utilized to adjust the ultrasound attenuation coefficient of the material to the desired level but have no substantial effect on MRI properties. The glass beads may be treated, such as by soaking in nitric acid to clean the surfaces thereof, to reduce the effect of any surface contamination on the glass beads on MRI properties.

An imaging phantom for use with at least ultrasound and MRI in accordance with the invention includes a phantom container and a tissue-mimicking material within the container, the tissue-mimicking material comprising at least two distinct sections in contact with each other, the tissue-mimicking material in the at least two sections in contact with each other including an aqueous mixture of large organic water soluble molecules, a copper salt, a chelating agent for binding the copper ions in the salt, and a gel-forming material, and wherein one of the sections includes glass beads intermixed therewith to provide a selected ultrasound attenuation coefficient to mimic muscle tissue, the glass beads treated to have a low effect on the MRI properties of the tissue-mimicking material. A section in contact with that section has glass beads or a larger size organ tissues such as prostate. The tissue-mimicking material may comprise at least two distinct sections in contact with each other, the two sections having first, small diameter glass or plastic beads (less than 20 μm diameter) intermixed therewith to provide a selected ultrasound attenuation coefficient, and wherein one of the sections includes larger beads (greater than 30 μm mean diameter) intermixed therewith to provide a selected backscatter coefficient therein. A preferred gel-forming agent is agar, and the dry weight concentration of agar in the section having glass beads therein is preferably higher than the dry weight concentration in the adjacent section to mimic the MRI properties of muscle tissue. A further section mimicking fat may also be in contact with one or both of the sections mimicking muscle tissue and organ tissue. Fat tissue may be mimicked by various materials including liquid vegetable oils such as safflower oil. In a region for mimicking fat, an open-cell reticulated mesh material that holds oil, such as the polyurethane material used in air filters, can be employed, with the liquid vegetable oil filling the interstices within the polyurethane material. Such a structure provides realistic ultrasound backscatter, simulating that due to the connective tissue matrix in real adipose tissue.

Further objects, features and advantages of the invention will be apparent from the following detailed description when taken in conjunction with the accompanying drawings.

DETAILED DESCRIPTION OF THE INVENTION

Figure 1:
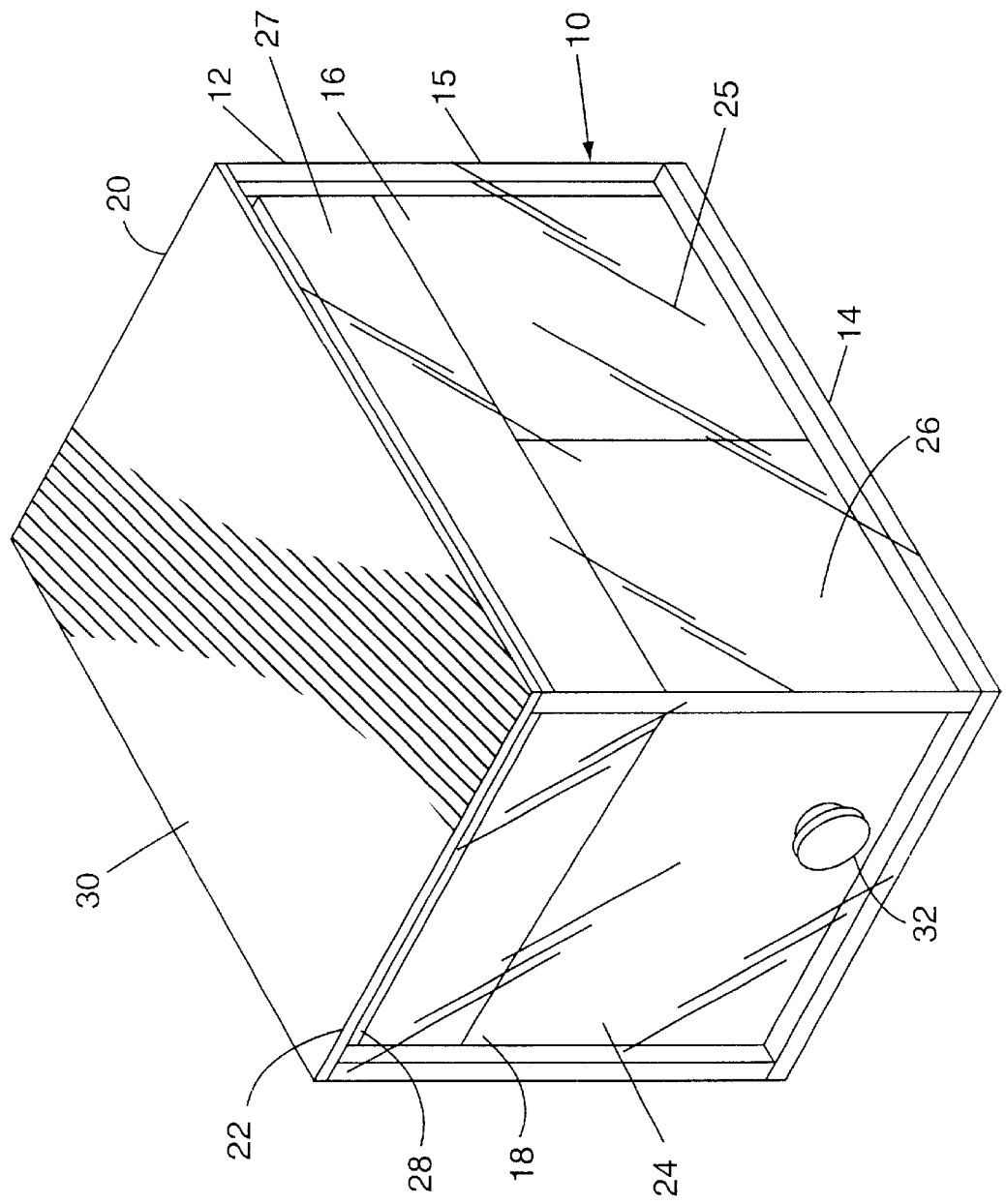
FIG. 1 is a perspective view of a multi-imaging modality phantom in accordance with the invention.

A multi-imaging modality phantom incorporating the tissue-mimicking material of the present invention is shown generally at 10 in FIG. 1 for purposes of illustrating the invention. The phantom 10 includes a container 12 having a bottom 14 and walls 15. Preferably the walls 15 include opposed faces 16, and opposed ends 18. Taken together, the bottom, faces, and ends 14, 16 and 18 form a hollow, box-like container structure. Margins of the walls 15 remote from the bottom 14 define a window 20. The window 20 is closed with an ultrasound-transmitting window cover 22. The window cover 22 may be made of any cohesive ultrasound transmitting material of suitable physical durability. A thin sheet of polyurethane or saran is preferred.

The phantom 10 further includes a body 24 of the tissue-mimicking material of the present invention. This material substantially fills the container 12 up to the level of the window 20, except as discussed below. The phantom body 24 includes several distinct sections, shown for illustration as three sections 25, 26 and 27, of the tissue-mimicking material of the present invention. As discussed further below, the three sections 25, 26 and 27 may comprise materials which mimic at least the MRI and ultrasound properties of three different body tissues; for example, the section 25 may have properties mimicking prostate parenchyma, the section 26 may mimic muscle, and the section 27 may mimic fat tissue.

The container 12 may be filled with the sections 25, 26 and 27 of tissue-mimicking material as desired, for example, in the manner described in U.S. Pat. No. 5,625,137. Although the sections 25, 26 and 27 have been shown for simplicity of illustration in FIG. 1 as rectangular blocks in contact with each other, as discussed further below, they may be and generally will be formed of other shapes, including shapes simulating human body structures such as a rounded inclusion of the material of the sections 25 surrounded by material of the sections 26 and 27.

The tissue-mimicking material of the present invention contains water and is subject to drying by escape of the water to the atmosphere. This can result in changes in the acoustic or NMR properties that make the material a less effective tissue mimicker. Consequently, the container 12 must be fluid tight and preferably also water vapor tight. The window cover 22 must include means for reducing water transfer therethrough. To this end, the window cover 22 may be made of a flexible plastic material that does not readily transmit water vapor. An alternative means for reducing water transfer through the window cover 22 includes a layer 28 of an oil-based gel that completely closes the window 20, adhering to the uppermost portions of the faces 16 and ends 18 in water and water vapor tight relation. The layer 28 of oil-based gel preferably is also covered with a thin and flexible plastic sheet 30 that forms part of the window cover 22 and that serves to form and protect the surface of the layer 28 of oil-based gel.

In practice, the bottom 14, faces 16, and ends 18 may be molded as a unit or formed of flat pieces of plastic or other material and be glued or otherwise joined so as to constitute the container 12. If the window cover 22 is to include the layer of oil-based gel, the plastic sheet 30 may first be glued or otherwise attached to the container 12 so as to close the window 20 in fluid-tight relation. At least one of the bottom 14, faces 16, or ends 18 includes a filling hole, shown at 32 and located in an end 18 of the ultrasound phantom 10 shown in FIG. 1. The layer 28 of oil-based gel may then be created by inserting through the filling hole 32 a sufficient quantity of the oil-based gel to make the layer 28, the oil-based material being in molten form. With the container 12 oriented so that the window 20 is downward most, the molten oil-based gel may then be allowed to cool and solidify. The exact thickness of the layer 28 is not critical. After the layer 28 of oil-based gel has been formed, the remainder of the container 12 may then be filled with the tissue-mimicking material by inserting the material in liquid form through the filling hole 32 and, for the solid form, allowing it subsequently to solidify as described above.

Exemplary prostate and muscle tissue-mimicking materials in accordance with the invention that may be used for the sections 25 and 26 contain agarose (Type A-4679, Sigma Chemical Co., St. Louis, Mo.), condensed milk (Diehl Company, Defiance, Ohio), distilled water deionized to 18 M-$\Omega$, n-propyl alcohol, $CuCl_2$ salt, EDTA (ethylenediaminetetraacetic acid, a chelating agent), and thimersal (preservative). $CuCl_2$ salt is used to lower T1. The use of a copper salt and chelating agent to lower T1 has been shown previously. J. R. Rice, et al., "Anthropomorphic $^1$H MRS Head Phantom," Medical Physics, Vol. 25, 1998, pp. 1145–1156. An appropriate chelating agent is EDTA. EDTA binds to the $Cu^{++}$ and prevents imobilization of the $Cu^{++}$ through the formation of metal-organic complexes with the rigid agarose or other gel that may be used. Thus, the use of $CuCl_2$ and EDTA together, forming mobile paramagnetic particles, results in a stable T1. Thimerosal prevents any bacterial invasion in the materials. Microscopic glass beads are added to the material mimicking muscle to augment the ultrasound attenuation. The differences in the materials mimicking prostate and muscle are the dry weight concentrations of agarose and the inclusion of glass beads in the material mimicking muscle. Fat tissue for the section 27 may be mimicked with vegetable oils such as pure safflower oil (The Hain Food Group, Gardena, Calif.) which may be suffused into an open cell mesh material that will hold oil, e.g., such as the materials used for air filters in air conditioners. A preferred example of such a material is polyurethane mesh, e.g., polyether polyurethane mesh, product code PDQZ-14A, "zether" natural mesh, pore size of 14 per linear inch, manufactured by Foamex, Eddystone, Pa. The oil is absorbed into this material and held in the interstices of the mesh. The values for the parameters specifying the composition of the three soft tissue-mimicking materials are given in Table 1.

TABLE 1

| Material | Composition of TM Material |
| --- | --- |
| Tissue-Mimicking Prostate (Section 25) | 50% (volume percent) condensed milk, 50% (volume percent) agarose solution (2% dry weight percent) and 7.9 cm$^3$ n-propyl alcohol per 100 cm$^3$ agarose solution, 0.103 g EDTA per 100 cm$^3$ of total volume, 0.06 g CUCl$_2$ per 100 cm$^3$ of total volume |
| Tissue-Mimicking Muscle (Section 26) | 50% (volume percent) condensed milk, 50% (volume percent) agarose solution (6% dry weight percent) and 7.9 cm$^3$ n-propyl alcohol per 100 cm$^3$ agarose solution, 0.0618 g EDTA per 100 cm$^3$ of total volume, 0.036 g CuCl$_2$ per 100 cm$^3$ of total volume, 5 g microscopic glass beads per 100 cm$^3$ total volume |
| Tissue-Mimicking Fat (Section 27) | Pure Safflower oil and polyurethane mesh (alternatively, pure safflower oil) |

The process of making the prostate and muscle tissue-mimicking materials is described as follows. Thimerosal is added to the condensed milk after which it is filtered. N-propyl alcohol (n-propanol) is added to deionized water (7.9% by volume). A known dry weight percent of dry agarose added is 2% for the material mimicking prostate and 6% for the material mimicking muscle. The resulting mixture is heated in a water bath until the agarose solution clarifies. The molten agarose solution is then cooled to 55° C. while the condensed milk is simultaneously heated to the same temperature. The agarose solution is then added to the condensed milk to make a 50-50 volume mixture. The mixture is stirred and air bubbles are discarded. 0.103 g per 100 cm$^3$ of EDTA and 0.06 g of CuCl$_2$ per 100 cm$^3$ of the mixture are then added and the mixture is stirred to ensure homogeneous distribution of all the constituent materials. In addition to all of the materials described above, microscopic glass beads are added to the material mimicking muscle. The glass beads are previously treated with nitric acid for a period of 24 hours to remove any paramagnetic impurities that might affect T1. They are then washed with water, dried, and homogenized by stirring. The purpose of homogenizing the glass beads is to ensure that they are uniformly distributed when added to the agar and milk mixture. Each material is then poured into a first cylinder which is placed on a mechanical rotator for a period of 24 hours to prevent the buildup of any gradients of components within the tissue-mimicking materials. Each first cylinder has an inner diameter of 7.6 cm with a 6 mm thick curved acrylic wall. 25 µm thick saran windows cover each end of the cylinder. The alternative tissue mimicking fat material (pure safflower oil) is made by pouring the oil into the cylinder. The preferred fat tissue-mimicking material is made by placing a 7.6 cm diameter, 2.5 cm thick disc of polyurethane mesh in the cylinder followed by pouring safflower oil into the mesh and gluing the second saran window in place.

For MRI, the parameters of interest are hydrogen T1 and T2 relaxation times. Measurements were performed on small samples in 5 mm diameter NMR tubes of tissue-mimicking prostate, muscle, and safflower oil (alternative fat tissue-mimicking material) using a 40 MHz Minispec spectrometer (Bruker, Canada) along with supporting equipment consisting of an IBM computer, a storage oscilloscope, and a constant temperature water bath maintained at a temperature slightly below 22° C. The 40 MHz spectrometer probe is maintained at 40° C. In order to make measurements at 22° C., the sample placed in the water bath initially is then inserted in the spectrometer probe. Data is acquired within 1.5 minutes to avoid significant temperature rise of the sample. It has been shown that the temperature rise within the first minute is less than 2° C. The spectrometer was interfaced with the computer which uses software from IBM Instruments (Danbury, Conn.) for pulse programming and data acquisition. The optimum pulse durations were found by maximizing the initial signal for a 90° pulse and minimizing the absolute value of the entire free induction decay (FID) for the 180° pulse.

An inversion recovery (IR) sequence was used to obtain the data for the longitudinal relaxation time. A relaxation time (TR) of at least five times the expected T1 was used. The T1 experiment was repeated ten times. Data reduction was done by curve fitting to an expression of the form:

$$M(t)=M_0(1-2 \exp(-t/T1)) \tag{1}$$

where M(t) is the instantaneous magnetization, $M_0$ is the initial longitudinal magnetization (thermal equilibrium), and t is the time at which each data point is acquired in the experiment. The uncertainty in the measurement of M(t) is calculated and this uncertainty is propagated to calculate the estimated uncertainty in T1.

The CPMG spin-echo pulse sequence was used to measure the transverse relaxation time. The relaxation delay (repetition time) was set to 7 s and data was acquired for τ (τ=one-half the echo time, TE) values of 25 µs, 125 µs, 250 µs, and 500 µs. 255 echo peaks were recorded in each CPMG sequence. The data obtained was fitted to a single exponential of the form:

$$M(t)=M_0 \exp(-t/T2) \tag{2}$$

where M(t) is the instantaneous magnetization at time t, $M_0$ is the initial magnetization and T2 is the transverse relaxation time.

For ultrasound phantom purposes, the material should exhibit the same speed of sound and ultrasonic attenuation as prostate tissue, skeletal muscle and fatty tissue. The backscatter parameter was adjusted by the addition of 45–53 µm glass beads, for example, as described in E. L. Madsen, et al., "Liquid or Solid Ultrasonically Tissue-mimicking Materials With Very Low Matter," Ultrasound in Med. and Bio., Vol. 24, 1998, pp.535–542.

The ultrasound parameters of the tissue-mimicking materials were measured as follows on the cylinders of tissue-mimicking material described above (one prostate, one muscle, one fat and one alternative fat). Tissue-mimicking material cylindrical samples are placed in a constant temperature water bath (maintained at 22° C.) between the transmitting transducer and receiving transducer. The parallel faces of the samples are maintained perpendicular to the ultrasound beam direction.

The speed of sound was measured by measuring the difference in the pulse arrival time for the cases in which the sample is present and absent between the transmitting transducer and the receiving hydrophone. The speed of sound in the tissue-mimicking material sample was then calculated relative to the speed of sound in distilled water. The ultrasonic attenuation coefficient at four discrete frequencies was measured with the same experimental setup. This was done by noting the pulse amplitudes when the sample is present and absent from the path of the ultrasound beam. Corrections for the nonzero thickness of thin plastic layers over the parallel sample faces are significant for frequencies above about 2 MHz and are included in the data reduction.

For evaluation of the materials for use as a CT phantom, the x-ray attenuation coefficient was measured with three different beam qualities at the Accredited Dosimetry Calibration Laboratory (ADCL), University of Wisconsin-Madison. The four sample cylinders discussed above were employed. The x-ray beams are calibrated and traceable to the National Institute of Standards and Technology (NIST). The beams used were M-150 and M-200 classified according to the filtration used with mean energies of 67 keV and 100 keV respectively. The M-150 x-ray beam is representative of a typical clinical CT beam. The x-ray system (Advanced X-ray, Atlanta, Ga.) uses a 14 kHz constant potential generator and has a tungsten anode with 3 mm inherent beryllium filtration.

The charge was collected with a spherical graphite walled ion chamber (Far West Technology, Calif.) and measured using an electrometer (Keithley Measurements, Inc., Cleveland, Ohio). The tissue-mimicking material sample was placed in the x-ray beam with its parallel face perpendicular to the direction of the x-ray beam. The attenuation coefficient was calculated by measuring the charge collected with and without the sample in the path of the x-ray beam and applying exponential attenuation to the beam due to the presence of the tissue sample.

$$I = I_0 \exp(-\mu_{eff} t) \quad (3)$$

where I is the charge collected with the sample in the beam, Io is the charge collected with the open beam, $\mu_{eff}$ is the effective attenuation coefficient, and t is the thickness of the sample.

Clinically, the CT number of a tissue-mimicking sample may be of more relevance than the measured effective attenuation coefficient. The CT number was measured using a Siemens CT scanner at 133 kVp and mean photon energy of 78 KeV. The tissue mimicking materials were scanned and the CT number measured from a selected region of interest from the CT images of the samples.

The foregoing materials are suitable for use in an anthropomorphic prostate phantom. In a phantom, where different components containing different concentrations of materials are in direct contact, it is a paramount importance that materials in one component do not cross the interface into an adjacent component. Such diffusion across the interfaces of various components of the phantom would lead to its degradation.

Figure 22:
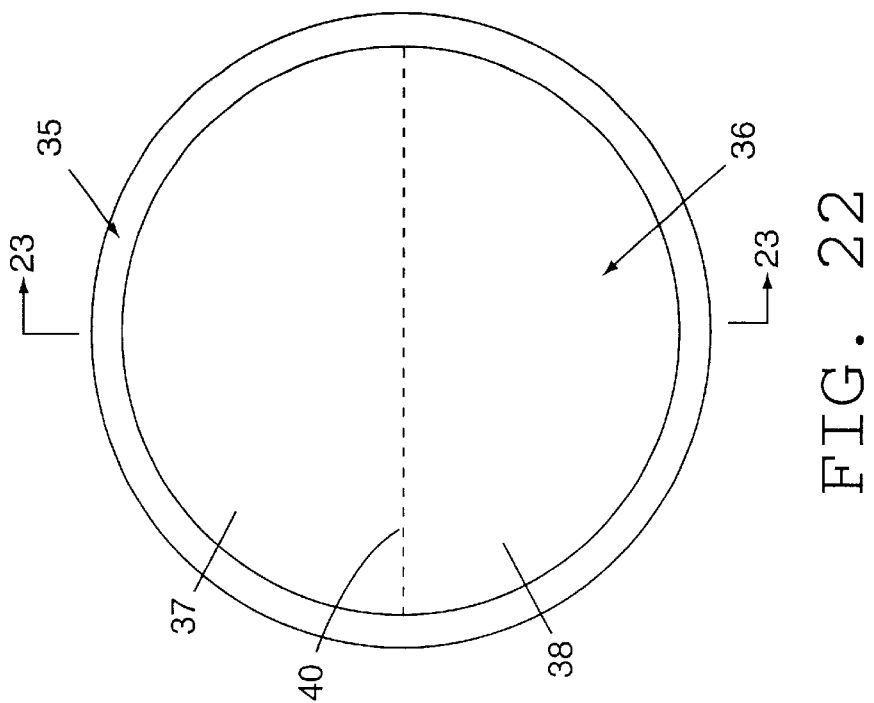
FIG. 22 is a top view of a test phantom for assessing the performance of various tissue-mimicking materials in contact with one another.
Figure 21:
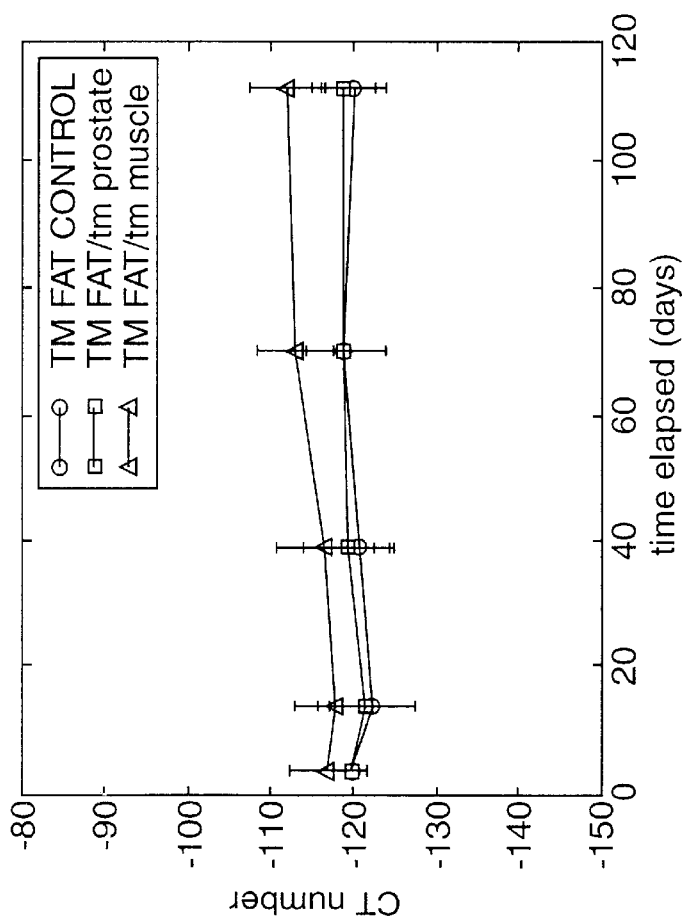
FIG. 21 are graphs of CT numbers over time for isolated fat mimicking material and for the same material in contact with prostate or muscle mimicking material.
Figure 23:
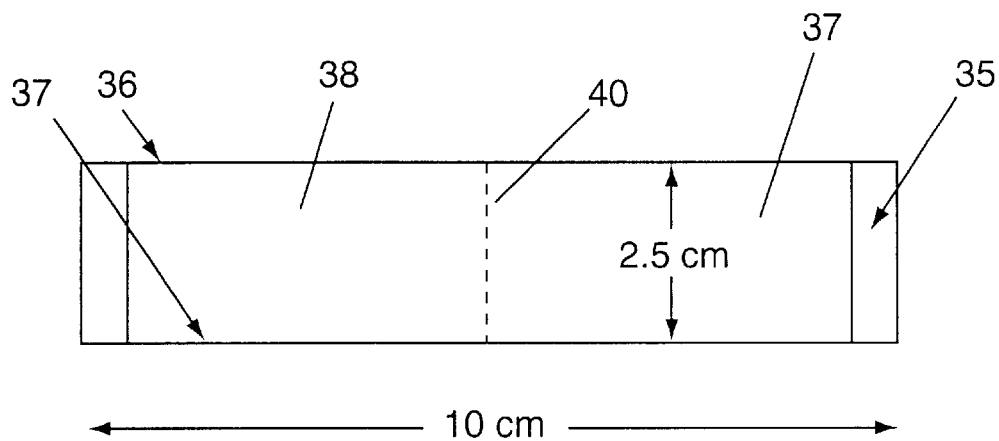
FIG. 23 is a cross-sectional view through the test phantom of FIG. 22 taken generally along the lines 23—23 of FIG. 22.

To test precisely this phenomenon, three test phantoms as shown in FIGS. 22 and 23 were constructed. These test phantoms had a container formed of a cylindrical wall 35 of acrylic plastic and top and bottom windows 36 and 37 of 25 micron thick saran. Each test phantom had a container of the type shown in FIGS. 22 and 23, but was first half filled with one type of tissue-mimicking material 37 and then with a second type of tissue-mimicking material 38 after the first tissue-mimicking material was allowed to stand and congeal for 24 hours, with the materials 37 and 38 in contact with each other at an interface 40. Each test phantom contained 50% (by volume) of one type of tissue-mimicking material and 50% of a different type of tissue-mimicking material. The first phantom contained material mimicking prostate tissue and material mimicking fat tissue; the second phantom contained material mimicking muscle tissue and material mimicking fat tissue; and the third phantom contained material mimicking prostate tissue and material mimicking muscle tissue. The composition of each of the long term stability test phantoms is listed in Table 2. In addition, three phantoms each filled with a single tissue-mimicking material were constructed to serve as controls and also to check the inherent stability of the tissue-mimicking materials.

TABLE 2

| Phantom | Volume Composition of Phantom |
|---|---|
| 1 | 50% TM Prostate, 50% alternative TM Fat |
| 2 | 50% TM Muscle, 50% alternative TM Fat |
| 3 | 50% TM Prostate, 50% TM Muscle |

To investigate if diffusion does occur across the interface between two different tissue-mimicking materials, the characteristic parameters were monitored using the long term stability phantoms described above over a period of months on each imaging modality. Measurements were made at monthly intervals of T1 and T2 relaxation times for MRI, speed of sound and ultrasonic attenuation for ultrasound, and CT numbers for computed tomography. This was done for each of the two different tissue-mimicking materials in contact in each of the three test phantoms, as well as in the control phantoms containing each individual tissue-mimicking material.

T1 and T2* were measured using a 1.5T GE Signa MRI scanner. T2* is a relaxation time that is unavoidably influenced by the measuring instrumentation, with $T2^* \leq T2$. To measure T1, six T1-weighted images were obtained with repetition times (TR) of 116 ms, 250 ms, 500 ms, 1000 ms, 2000 ms, and 4000 ms respectively with an echo time (TE) of 15 ms. Regions of interest were selected for each tissue-mimicking material in all three phantoms, and the mean pixel values along with the standard deviations were recorded. The data was curve fitted to an exponential of the form of Equation 1. T2* was measured by using a CPMG multi-echo pulse sequence with TR=2000 ms and echos were acquired at 20 ms, 40 ms, 60 ms and 80 ms. This data was curve fitted to an equation of the form of Equation 2.

The speed of sound and ultrasonic attenuation for the long term stability phantoms were measured in the same manner as was previously described. The phantom was placed in between the transmitting transducer and the receiving hydrophone in such a way that the ultrasound beam passed through only one of the two tissue-mimicking materials in the phantom. This was then repeated for the second tissue-mimicking material in the phantom. The CT number was monitored for each tissue-mimicking material in the three long term stability phantoms through sequential CT scans. Measurements of the same parameters were also made with the control phantoms on all three imaging modalities. These measurements were repeated at regular intervals over a five month period on each imaging modality to assess long term stability.

T1 and T2 relaxation times for actual human tissue is shown in Table 3. The T1 and T2 values measured using a relaxometer for the tissue-mimicking (denoted TM in the tables) materials are shown in Table 4 and Table 5 respectively (in Table 5, T2 values are indicated with ± uncertainties), and T1 and T2* times measured using a 1.5 T GE Signa MRI scanner are given in Table 11 and Table 12, respectively. Relaxometer T2 times were found to vary with the echo time (2τ). T1 was calculated using Equation 1. The uncertainty in the T1 measurement was determined by propagating the standard deviation associated with $M_{(t)}$ measurements obtained from repeating the T1 experiment (using IR pulse sequence) ten times. It must be noted that although the samples are maintained in a water bath at 22° C. there may be a slight temperature rise (say 2° C.) in them because the 40 MHz spectrometer is maintained at 40° C. Data obtained from the T2 experiment was curve fitted in a least squares manner to Equation 2 to obtain T2 and the uncertainty associated with it.

Good agreement is found between the measured values for the tissue-mimicking materials and the literature values for actual human tissue shown in Table 3. It is important to note that T1 depends somewhat on the Larmor frequency, typically with a square-root-of-frequency dependence. Measurements were done with a 40 MHz spectrometer and most clinical MRI units operate at a Larmor frequency of 60 MHz.

Reproducibility of the relaxation times is an indication of the overall precision of the measurement. The T1 measured by relaxometer for tissue-mimicking prostate was 937 ms with a standard deviation of 13 ms. T1 times for tissue-mimicking muscle and tissue-mimicking fat are shown in Table 4. T2 for each tissue-mimicking material was measured for different τ values. The average T2 for tissue-mimicking prostate was 88.0 ms with a standard deviation of 1.2 ms. Similarly the average T2 values for tissue-mimicking muscle and tissue-mimicking fat were measured as 36.7 ms and 154.4 ms with a standard deviations of 0.7 ms and 3.4 ms respectively.

TABLE 3

| Human tissue-type | Temp. (° C.) | In vivo? | Frequency (MHz) | T1 (ms) | T2 (ms) |
|---|---|---|---|---|---|
| prostate | 40 | no | 20 | 808 | 98 |
| muscle | 37 | yes | 6 | — | 47 ± 3 |
| " | 37 | yes | 15 | 514 ± 138 | — |
| " | 37 | no | 43.5 | 650 – 800 | — |
| fat | 37 | yes | 12 | 209 ± 17 | 135 ± 16 |
| " | 37 | yes | 15 | 266 ± 45 | 57 ± 3 |

TABLE 4

| Sample | T1(ms) |
|---|---|
| TM prostate | 937 ± 13 |
| TM muscle | 686 ± 9 |
| TM fat (pure safflower oil) | 207 ± 6 |

TABLE 5

| τ (μs) | TM prostate T2 | TM muscle T2 | TM fat T2 |
|---|---|---|---|
| 25 | 84.2 ± 0.2 | 37.4 ± 0.1 | 154.8 ± 0.4 |
| 125 | 91.1 ± 0.3 | 39.1 ± 0.3 | 154.6 ± 0.7 |
| 250 | 91.5 ± 0.5 | 35.3 ± 0.3 | 149.6 ± 2.9 |
| 500 | 85.3 ± 1.0 | 35.1 ± 0.5 | 158.6 ± 1.6 |

Figure 2:
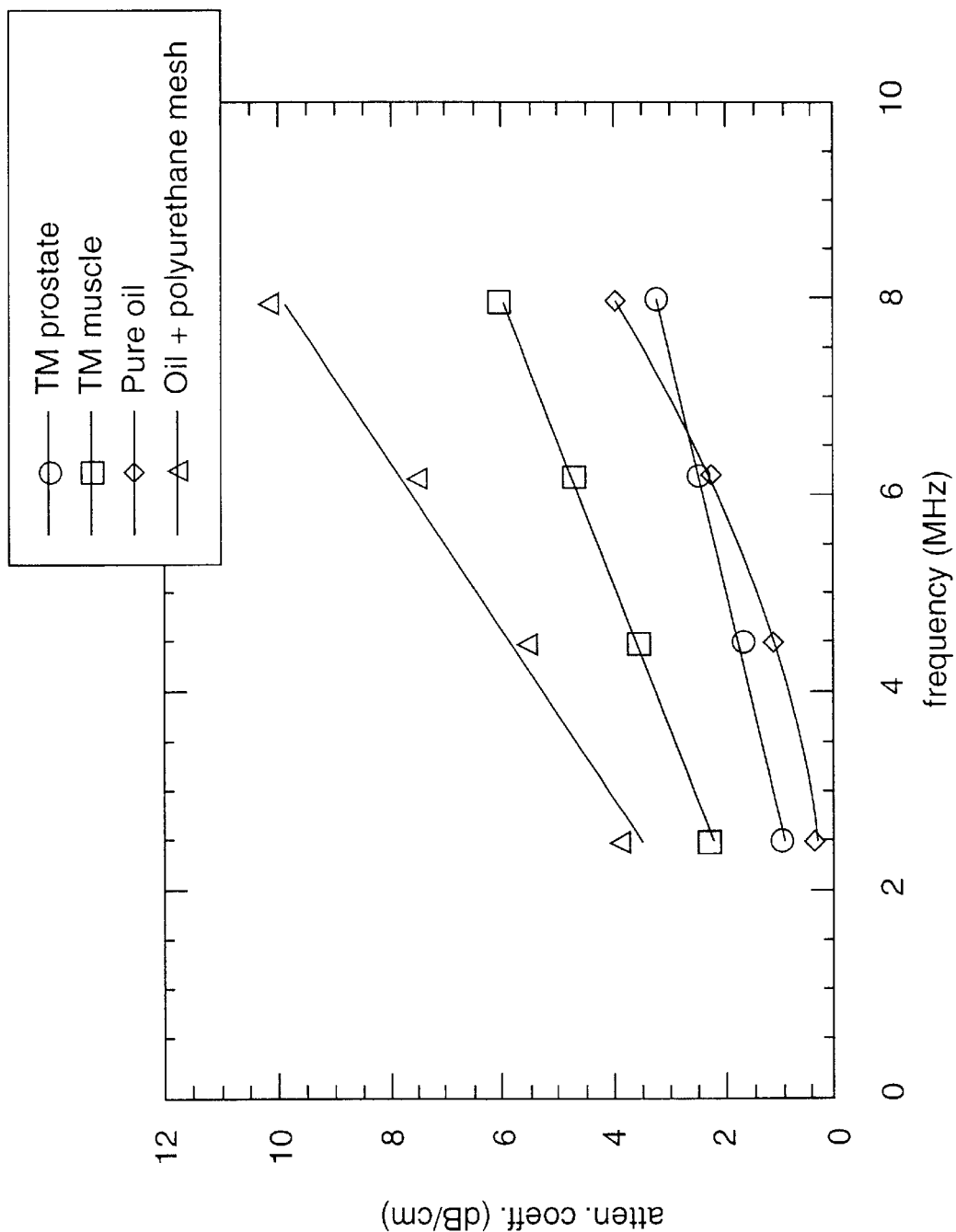
FIG. 2 are graphs illustrating ultrasound attenuation dependence on frequency for materials mimicking prostate, muscle and fat tissue.

Ultrasound attenuation was measured at four different transducer frequencies 2.5, 4.5, 6.2, and 8.0 MHz. FIG. 2 shows the ultrasonic attenuation dependence on frequency for each of the TM materials.

A compilation of ultrasound propagation speeds and attenuation values for human soft tissues relevant to a prostate phantom is shown in Tables 6 and 7, respectively. The corresponding measured values at 22° C. for the tissue-mimicking materials developed are shown in Table 8. More detailed attenuation values for human and animal fat are given in Table 9. Data for prostate tissue was not found in the literature so only values for muscle and fat are given in Tables 6, 7 and 9. Sound speeds in muscle and fat correspond reasonably well with those in the tissue-mimicking versions. Attenuation coefficient/frequency values in muscle are a little higher than in the TM muscle. Attenuation coefficient/frequency values for fat (Table 9—see values in parentheses) are comparable to those in TM fat (safflower oil plus polyurethane mesh).

Regarding ultrasound backscatter coefficients, comparison of relative values for prostate muscle and fat in ultrasound patient scans with relative values in the TM materials (using TM fat with oil and polyurethane) show good agreement; this is important for use in anthropomorphic phantoms.

TABLE 6

| Human Tissue Type | Temperature (° C.) | In vivo? | Speed of sound (m/s) |
|---|---|---|---|
| muscle | 37 | yes | 1580 |
| fat | 35 | no | 1476 |

TABLE 7

| Human Tissue Type | Temperature (° C.) | In vivo? | Frequency (MHz) | Attenuation coefficient/frequency (dB/cm/MHz) |
|---|---|---|---|---|
| muscle | 37 | yes | 4.3 | 1.10 ± 0.10 |
| fat | room | no | 4–8 | 0.5–1.6 |

TABLE 8

| Material | Ultrasound Atten. Coeff. in dB/cm (Atten. Coeff./freq. In dB/cm/MHz) | | | | Speed of Sound (m/s) |
|---|---|---|---|---|---|
| | 2.5 MHz | 4.5 MHz | 6.2 MHz | 8.0 MHz | |
| TM prostate | 0.97 ± 0.20 | 1.62 ± 0.20 | 2.41 ± 0.20 | 3.13 ± 0.20 | 1537 ± 2 |
| | (0.39 ± 0.08) | (0.36 ± 0.04) | (0.37 ± 0.03) | (0.39 ± 0.03) | |
| TM muscle | 2.25 ± 0.20 | 3.18 ± 0.20 | 4.61 ± 0.20 | 5.92 ± 0.20 | 1544 ± 2 |
| | (0.9 ± 0.08) | (0.77 ± 0.04) | (0.71 ± 0.03) | (0.74 ± 0.03) | |
| TM fat (pure oil) | 0.4 ± 0.20 | 1.10 ± 0.20 | 2.18 ± 0.20 | 3.88 ± 0.20 | 1464 ± 2 |
| | (0.16 ± 0.08) | (0.24 ± 0.04) | (0.34 ± 0.03) | (0.49 ± 0.03) | |

TABLE 8-continued

| Material | Ultrasound Atten. Coeff. in dB/cm (Atten. Coeff./freq. In dB/cm/MHz) | | | | Speed of Sound (m/s) |
| --- | --- | --- | --- | --- | --- |
| | 2.5 MHz | 4.5 MHz | 6.2 MHz | 8.0 MHz | |
| TM fat (pure oil + polyurethane mesh) | 3.86 ± 0.20 (1.54 ± 0.08) | 5.48 ± 0.20 (1.22 ± 0.04) | 7.46 ± 0.20 (1.20 ± 0.03) | 10.07 ± 0.20 (1.26 ± 0.03) | 1468 ± 2 |

TABLE 9

| Tissue type | Temperature (° C.) | Frequency (MHz) | Atten. Coeff. (dB/cm) | Atten Coeff./freq. (dB/cm/MHz) |
| --- | --- | --- | --- | --- |
| Human | 37 | 5 | 2.3 | 0.46 |
| Human | 18.2 | 4 | 4.2 | 1.05 |
| Human | 18.2 | 5.6 | 6.1 | 1.09 |
| Bovine | 37 | 5 | 6.0 | 1.20 |
| Bovine | 37 | 6 | 7.0 | 1.17 |
| Bovine | 37 | 7 | 8.0 | 1.14 |
| Porcine | 37 | 4 | 5.5 | 1.38 |
| Porcine | 37 | 6 | 8.5 | 1.42 |
| Porcine | 37 | 8 | 12.5 | 1.56 |
| Porcine | 37 | 4 | 3 | 0.75 |
| Porcine | 37 | 6 | 4.9 | 0.82 |
| Porcine | 37 | 7 | 7 | 1.0 |

CT numbers obtained with a CT scanner at 133 kVp and mean photon energy of 78 keV, and x-ray attenuation coefficients measured with the ADCL system for two different effective energies, are shown in Table 10 for the four tissue-mimicking materials. The x-ray beams are classified according to the filtration present in the beam. For comparison with CT numbers in corresponding human tissues, see Table 11 (i.e., compare the right-most columns of Tables 10 and 11).

TABLE 10

| Material | Attenuation coefficient (cm$^{-1}$) | | CT number at 78 keV (133 kVp) on UW radiotherapy Ct scanner |
| --- | --- | --- | --- |
| | M-150, E = 67 keV | M-200, E = 100 keV | |
| TM prostate | 0.204 ± 0.008 | 0.173 ± 0.008 | 47 ± 5 |
| TM muscle | 0.214 ± 0.009 | 0.179 ± 0.008 | 88 ± 5 |
| TM fat (oil and polyurethane) | — | — | −115 ± 3 |
| Alternative TM fat (pure oil) | 0.179 ± 0.008 | 0.160 ± 0.007 | −120 ± 4 |

TABLE 11

CT Numbers for In Vivo Human Soft Tissues.

| Human Soft Tissue | CT number at mean photon energy of 62 keV[+] | CT number at 78 keV (133 kVp) on UW Siemens Radiotherapy CT Scanner[++] |
| --- | --- | --- |
| Prostate | Not measured | 36 ± 10 |
| Muscle | 59 | 61 ± 7 |
| Fat | −114 | −97 ± 9 |

[+]G. D. Fullerton, "Fundamentals of CT Tissue Characterization," Medical Physics of CT and Ultrasound: Tissue Imaging and Characterization, edited by G. D. Fullerton and J. A. Zagzebski, page 129, 1984.
[++]Means and standard deviations on two human subjects. Eighteen CT numbers averaged for each mean.

The degree of correspondence of CT numbers between the tissue-mimicking materials and in vivo human tissue values can be assessed using Tables 9 and 10. The level of agreement is reasonably good, comparing CT numbers attained under identical conditions (same scanner, kVp and mean photon energy). For TM prostate, CT#=47±5, while for human tissue, CT#=36±10. For TM muscle, CT#=61±7. For TM fat (oil only), CT#=−120±4 and TM fat (oil and polyurethane), CT#=−115±3, while human fat, CT#=−97±9. Thus, the contrast between TM materials mimics that for the actual in vivo human tissues rather well.

TABLE 12

| Sample | T1(ms) |
| --- | --- |
| TM prostate | 1032 ± 8 |
| TM muscle | 750 ± 2 |
| TM alternative fat (pure oil + polyurethane mesh) | 306 ± 15 |
| TM fat (pure safflower oil) | 302 ± 16 |

TABLE 13

| Sample | T2*(ms) |
| --- | --- |
| TM prostate | 44.3 ± 0.1 |
| TM muscle | 19.1 ± 0.1 |
| TM fat (pure oil + polyurethane mesh) | 30 ± 1 |
| Alternative TM fat (pure oil) | 40 ± 3 |

FIGS. 3–21 show the results of the long term stability measurements on each phantom sample for MRI, ultrasound, and CT. The initial concentrations (at the time of production) of $Cu^{++}$ and EDTA were the same in the prostate and muscle mimicking material. There is no change in the ultrasound and CT parameters as well as the T2* of the tissue-mimicking materials in the long term stability phantoms. The graphs for T1 however (see FIGS. 3 and 4) show changes in the T1 relaxation times for the phantom containing TM prostate and TM muscle. The T1 instability was attributed to the possibility that, for tissue-mimicking muscle and tissue-mimicking prostate in direct contact, the equilibrium concentrations of $Cu^{++}$ and EDTA in the two materials are not equal. Three new long term stability phantoms were constructed in which the ratio of the concentration of $Cu^{++}$/EDTA in TM muscle to that in TM prostate was lowered to 0.6, 0.7 and 0.8. FIG. 5 shows the time dependencies of T1 of tissue-mimicking prostate and tissue-mimicking muscle in the new long term stability phantoms.

MRI, ultrasound and CT parameters were monitored for tissue-mimicking materials in direct contact with each other in the long term stability phantoms with equal concentrations of $Cu^{++}$/EDTA in tissue-mimicking prostate and tissue-mimicking muscle. The ultrasound attenuation, speed of sound and CT number did not show any variation over a course of five months relative to the controls (containing isolated tissue-mimicking materials) which were monitored in the same manner. T2* values obtained with the MR scanner did not show any change over the same period of time. It must be noted that the values for T2* obtained are significantly lower than the true T2 values of the tissue-mimicking materials measured with a relaxometer. T2* was measured using a multi-echo sequence where the successive 180° refocusing pulses are not exact. Hence, the spins towards the edge of the slice may or may not see the 180° pulse. As a result, the slice thickness effectively decreases with each successive 180° pulse and there is a loss of signal with each successive echo. Since T2* does not change with time, it can be assumed that T2 does not change either.

Figure 3:
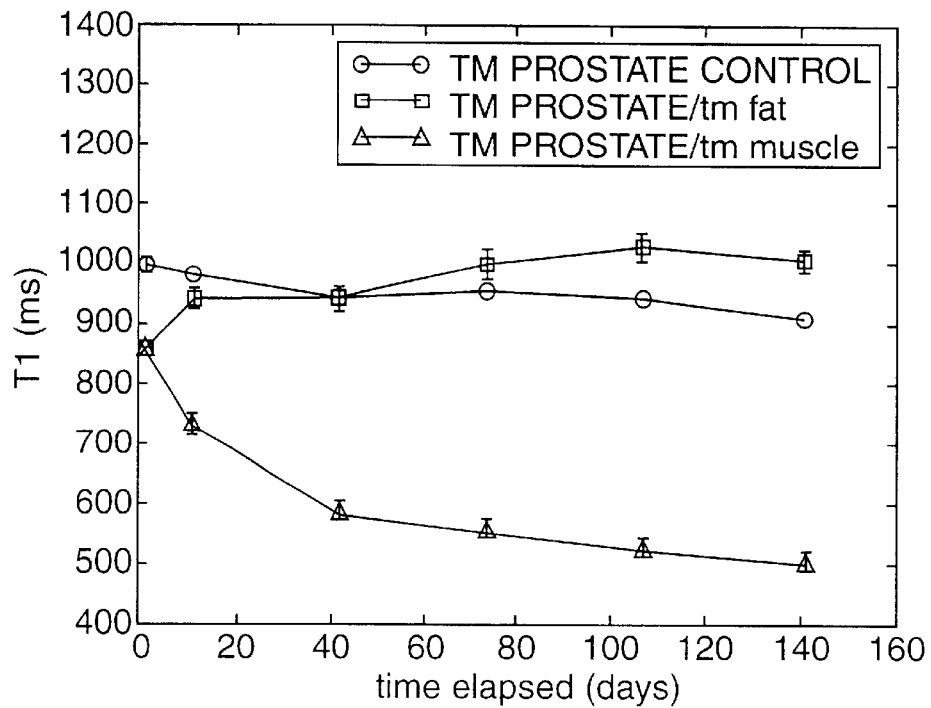
FIG. 3 are graphs illustrating T1 values over time for prostate mimicking material by itself and for the same material in contact with muscle and fat mimicking material.
Figure 4:
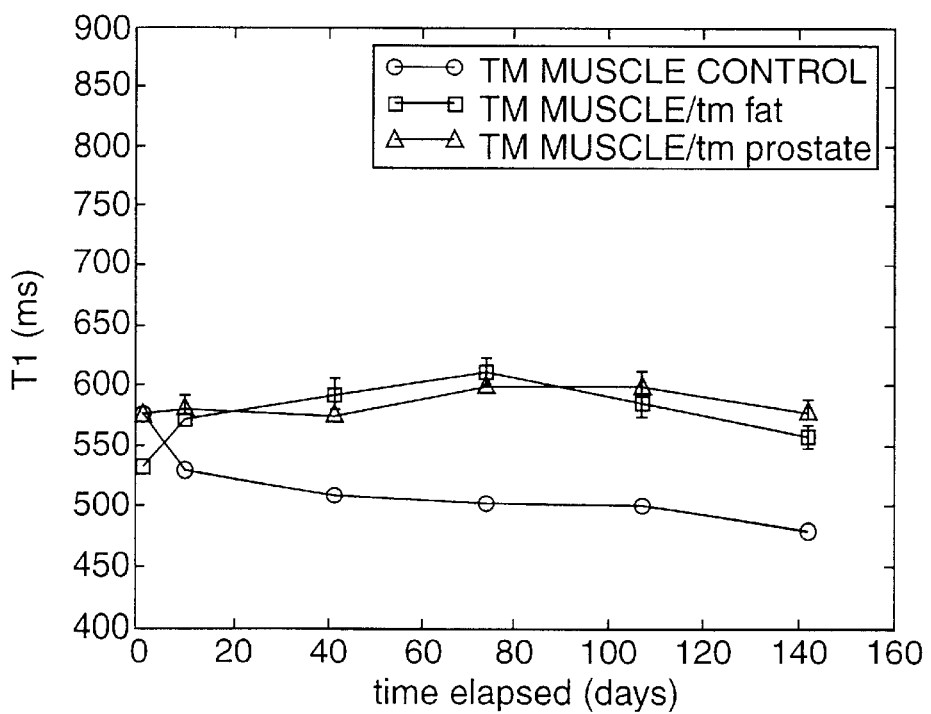
FIG. 4 are graphs illustrating T1 values over time for muscle mimicking material by itself and for the same material in contact with prostate and fat mimicking material.
Figure 5:
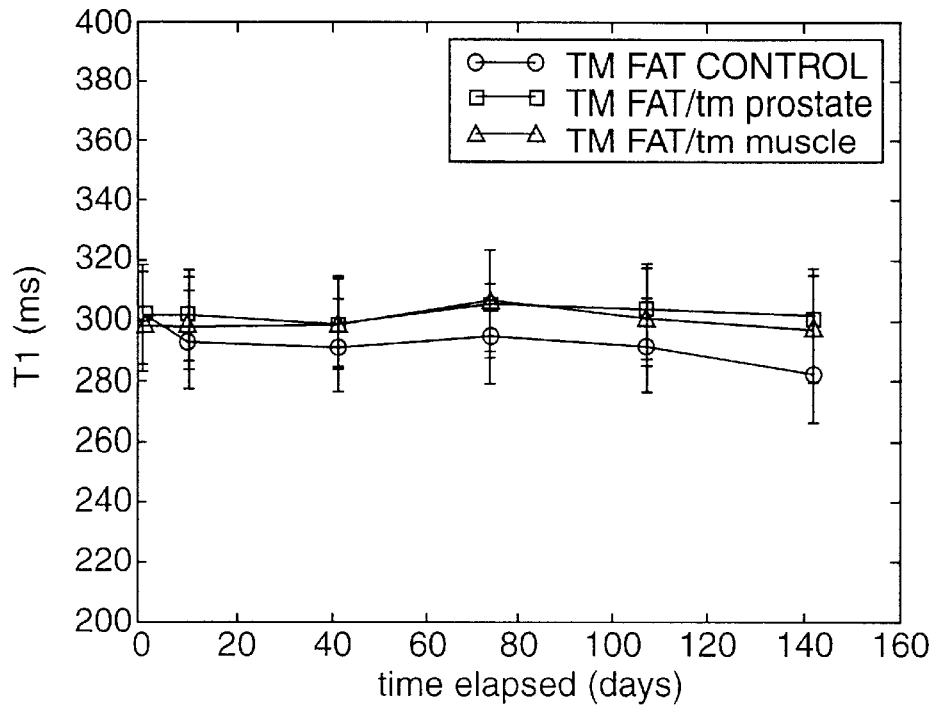
FIG. 5 are graphs illustrating T1 values over time for fat mimicking material by itself and for the same material in contact with prostate and muscle mimicking material.
Figure 6:
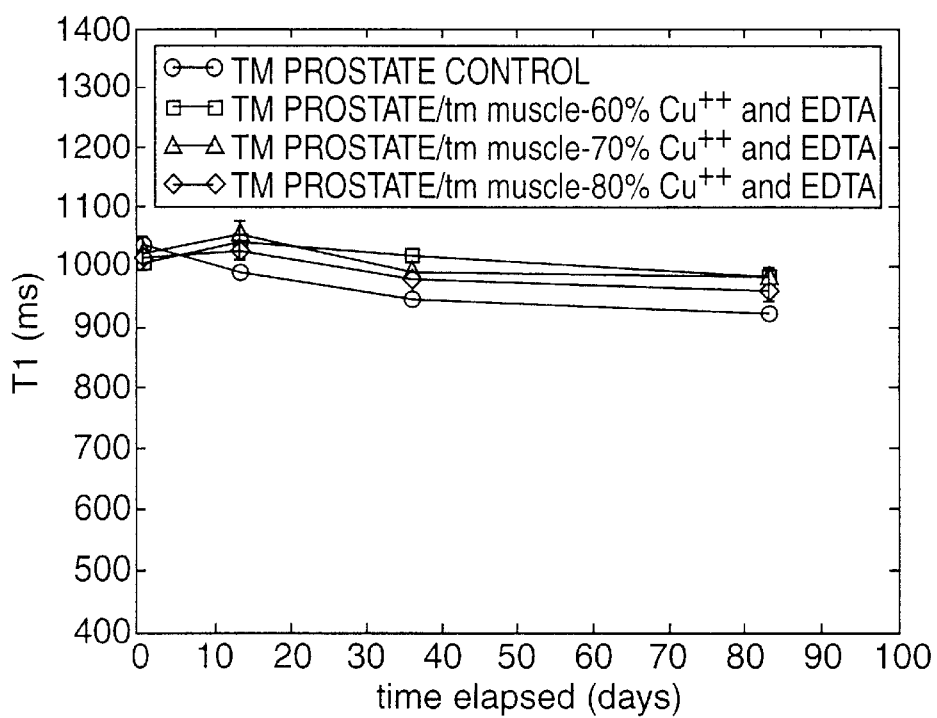
FIG. 6 are graphs illustrating T1 values over time for isolated prostate mimicking material (not in contact with any other tissue-mimicking material) and for the same material in contact with muscle mimicking material, at various concentrations of Cu++ and EDTA in the muscle mimicking material as a percent of that in the isolated prostate tissue-mimicking material and that initially in the prostate material in contact with the muscle mimicking material.
Figure 7:
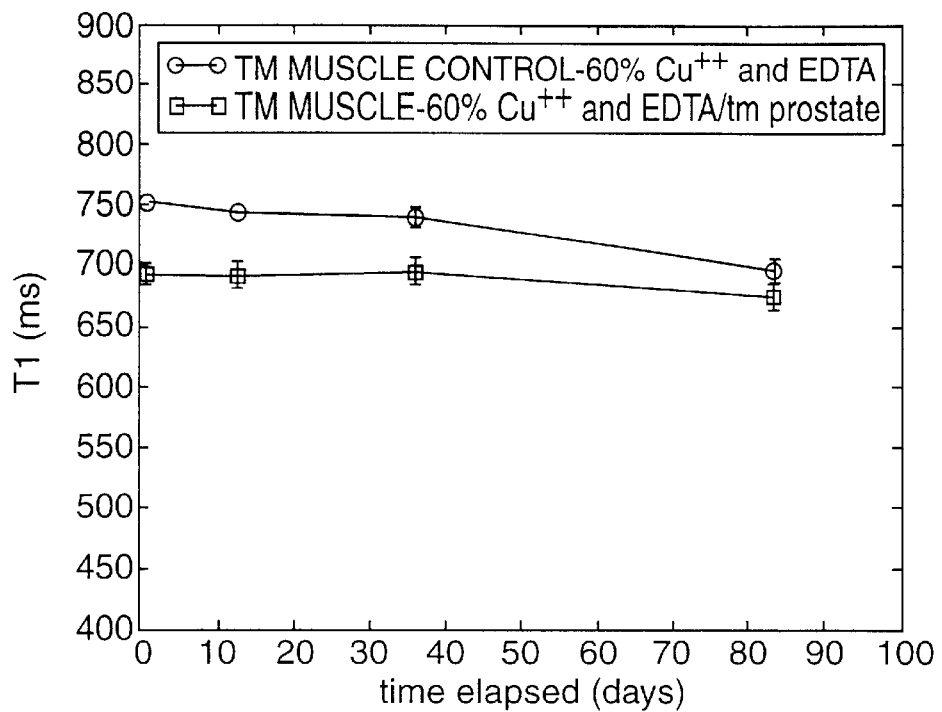
FIG. 7 are graphs illustrating T1 values over time for isolated muscle mimicking material and for the same material in contact with prostate mimicking material.
Figure 8:
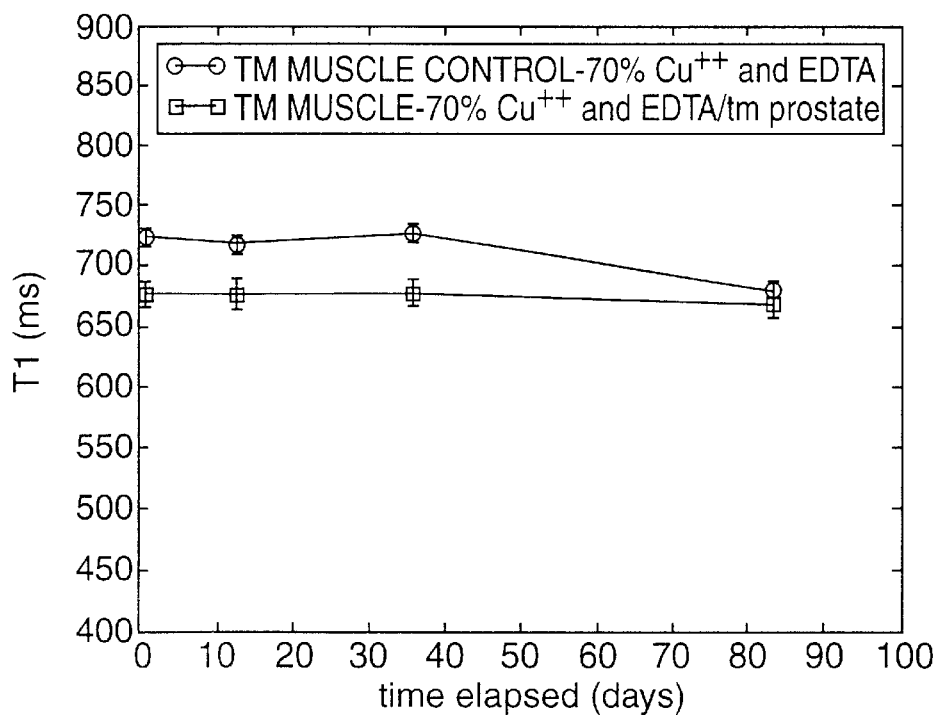
FIG. 8 are graphs illustrating T1 values over time for isolated muscle mimicking material at 70% Cu++ and EDTA relative to concentrations in the prostate mimicking material and for the same material in contact with prostate mimicking material.
Figure 9:
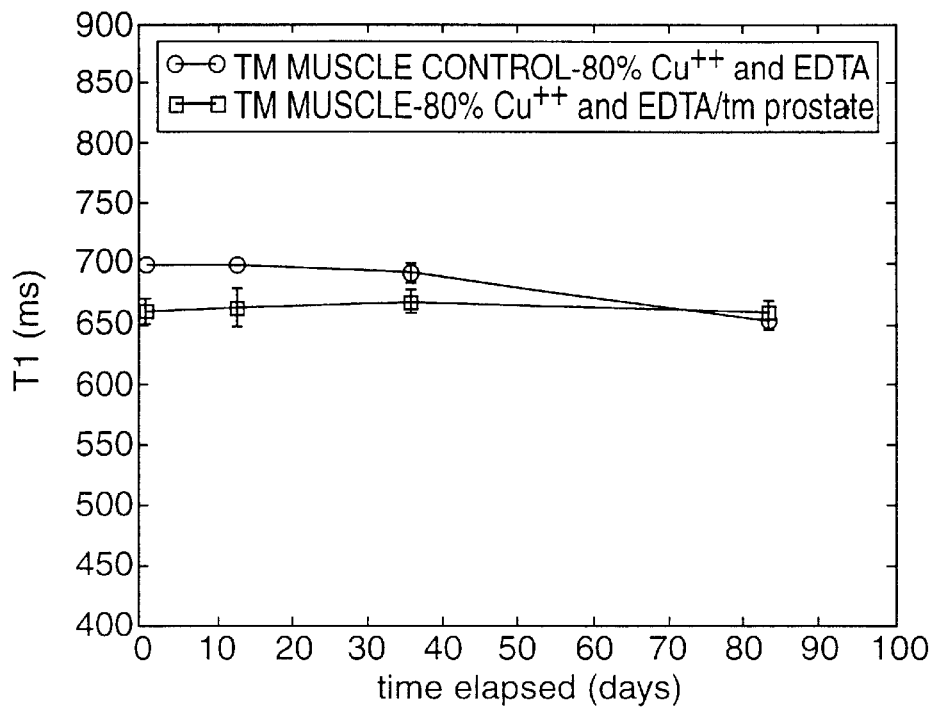
FIG. 9 are graphs illustrating T1 values over time for isolated muscle mimicking material at 80% Cu++ and EDTA relative to concentrations in the prostate mimicking material and for the same material in contact with prostate mimicking material.
Figure 10:
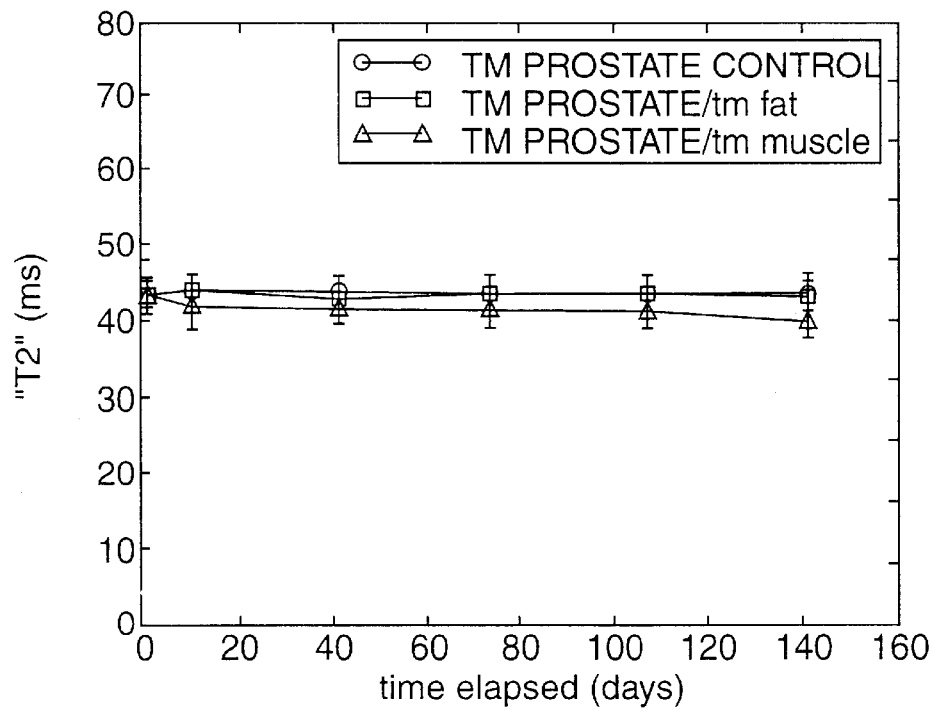
FIG. 10 are graphs illustrating T2 values over time for isolated prostate mimicking material by itself and for the same material in contact with either fat or muscle mimicking material.
Figure 11:
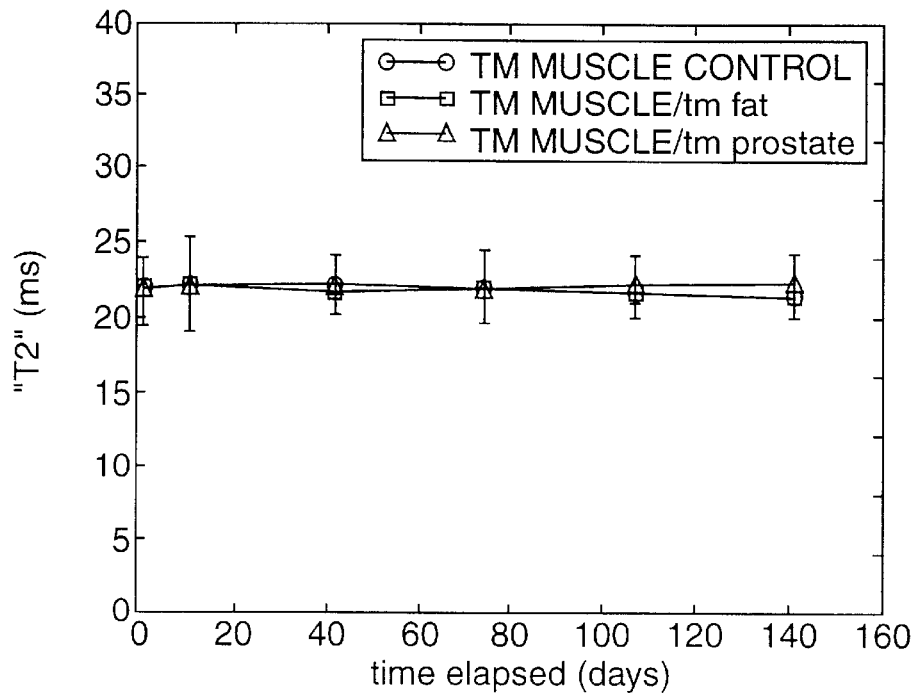
FIG. 11 are graphs illustrating T2 values over time for muscle mimicking material by itself and for the same material in contact with fat and prostate mimicking material.
Figure 12:
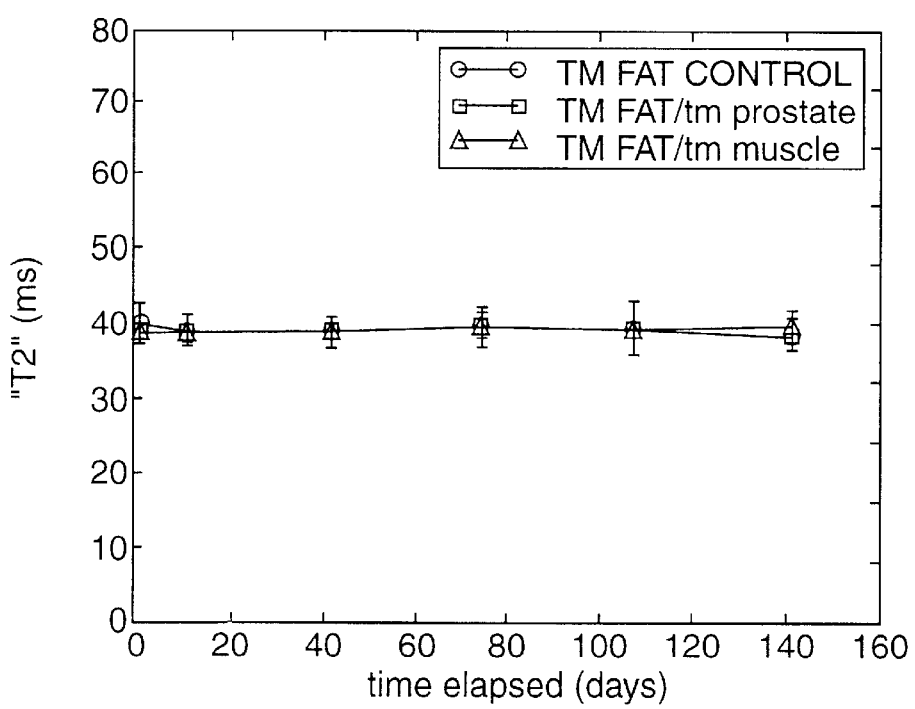
FIG. 12 are graphs illustrating T2 values over time for fat mimicking material by itself and for the same material in contact with prostate and muscle mimicking material.
Figure 13:
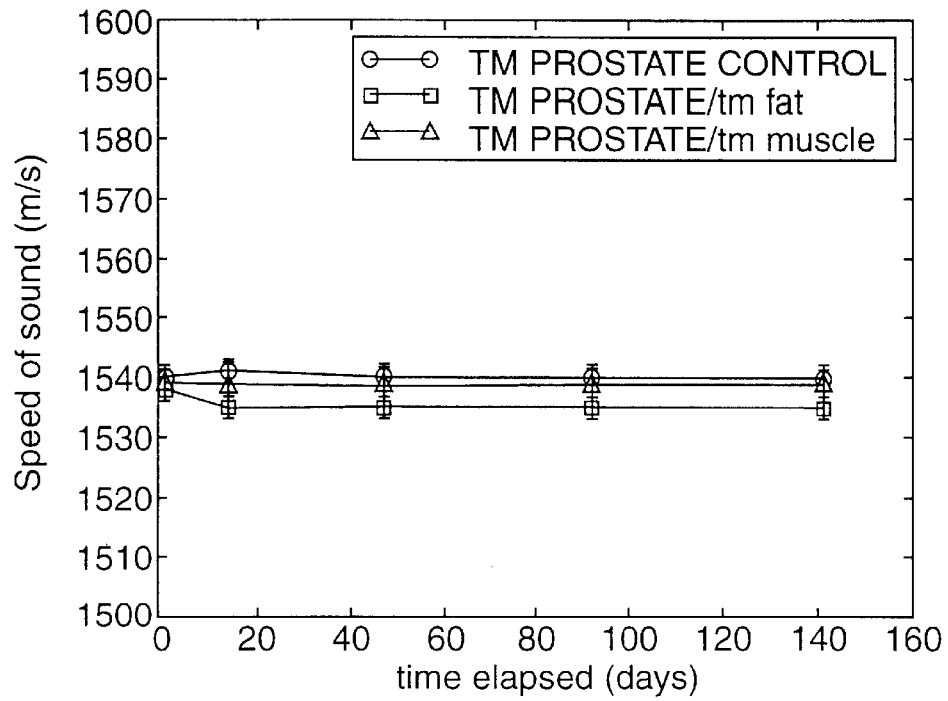
FIG. 13 are graphs of the speed of sound over time in prostate mimicking material by itself and for the same material in contact with fat and muscle material.
Figure 14:
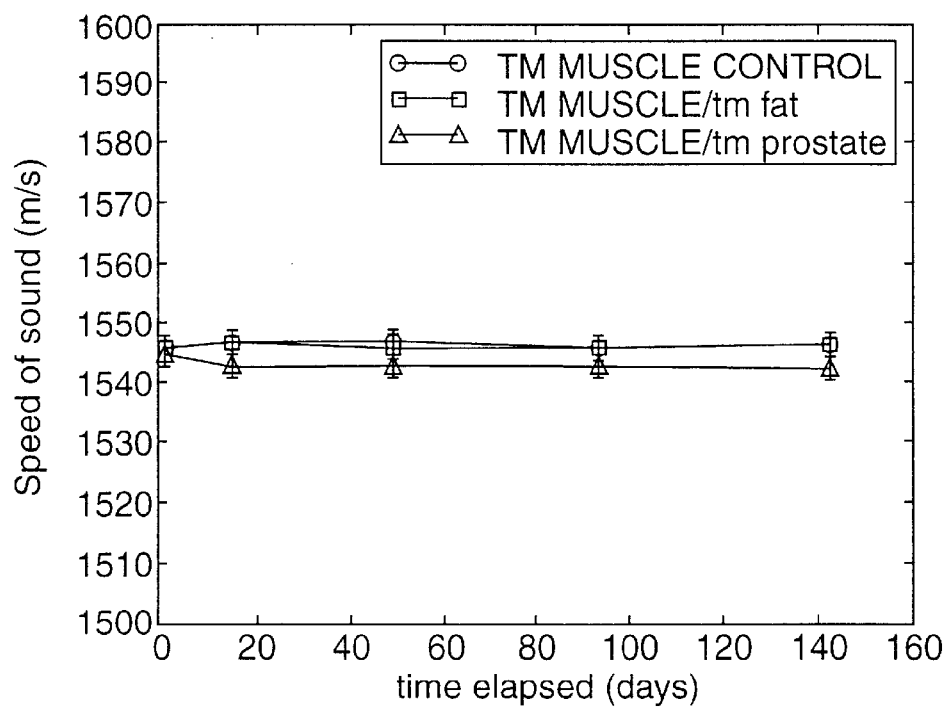
FIG. 14 are graphs of the speed of sound over time in muscle mimicking material by itself and for the same material in contact with fat and prostate mimicking material.
Figure 15:
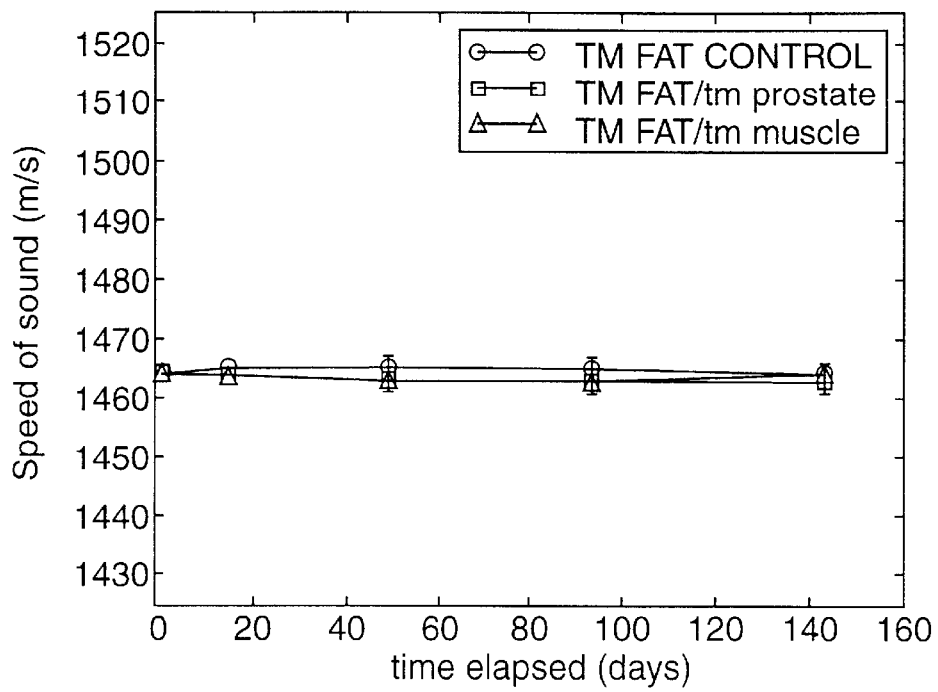
FIG. 15 are graphs of the speed of sound over time in fat mimicking material by itself and for the same material in contact with prostate and muscle mimicking material.
Figure 16:
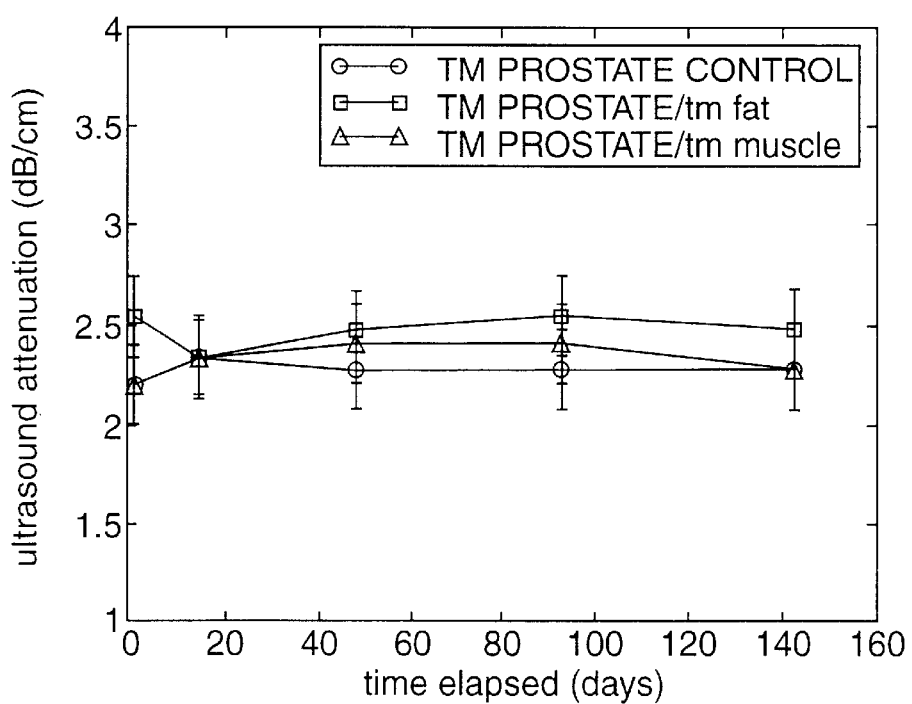
FIG. 16 are graphs of ultrasound attenuation over time for prostate mimicking material by itself and for the same material in contact with fat and muscle mimicking material.
Figure 17:
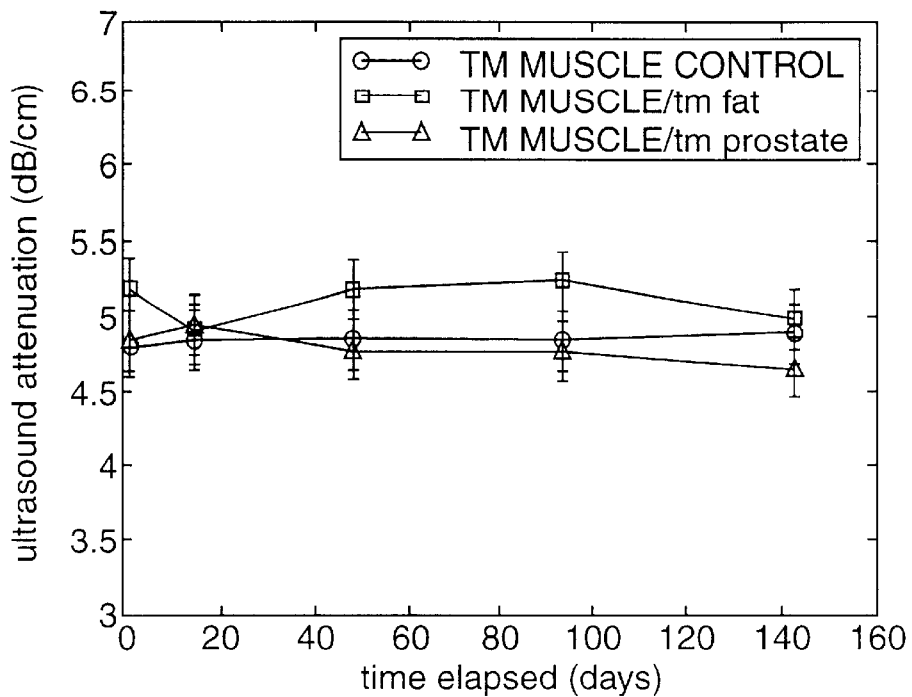
FIG. 17 are graphs of ultrasound attenuation over time for muscle mimicking material by itself and for the same material in contact with prostate and fat mimicking material.
Figure 18:
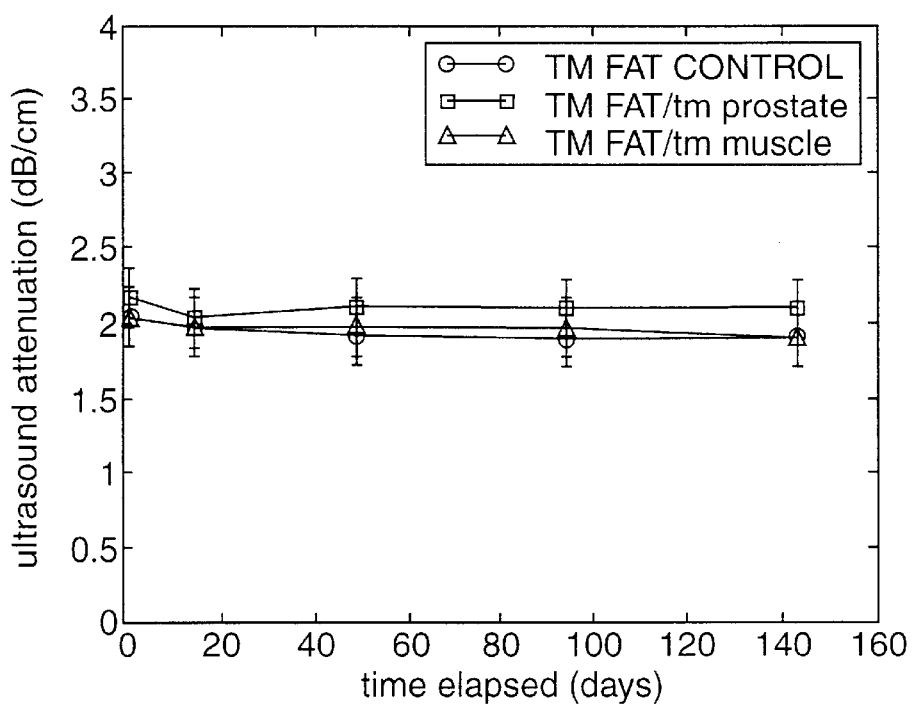
FIG. 18 are graphs of ultrasound attenuation over time for fat mimicking material by itself and for the same material in contact with prostate and muscle mimicking material.
Figure 19:
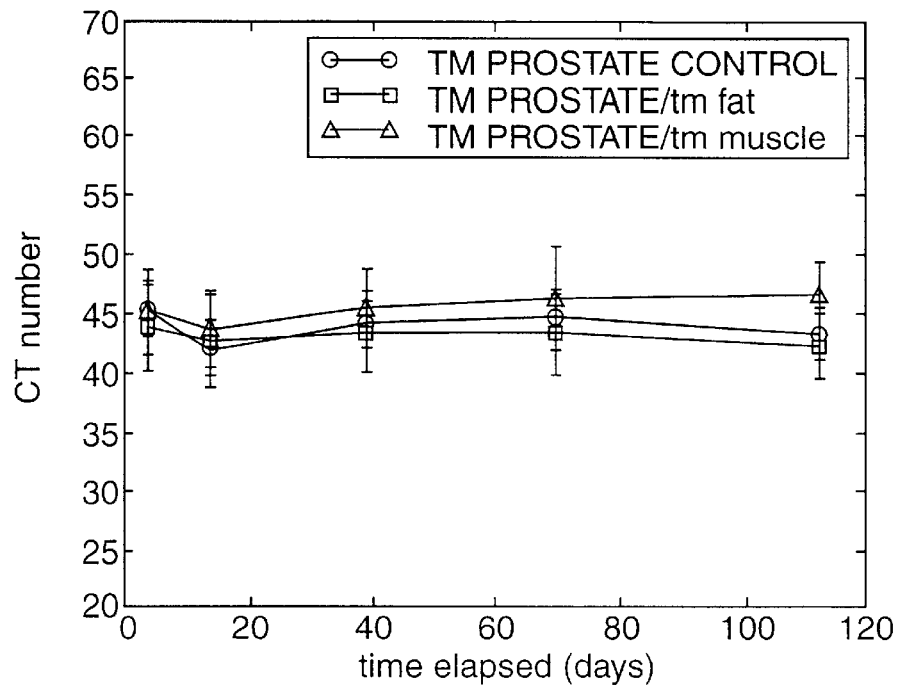
FIG. 19 are graphs of CT numbers over time for prostate mimicking material by itself and for the same material in contact with muscle and fat mimicking material.
Figure 20:
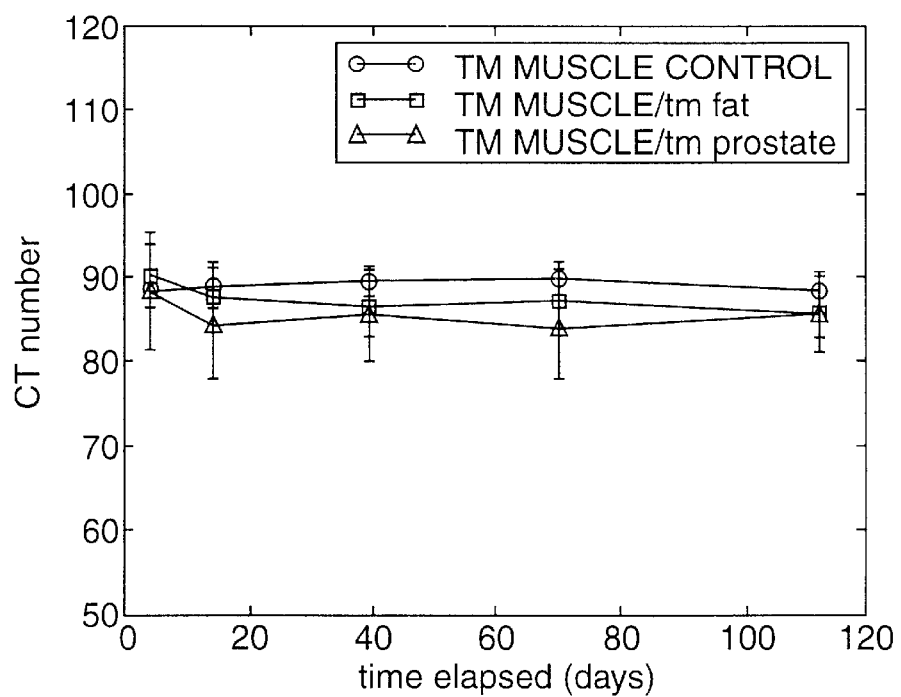
FIG. 20 are graphs of CT numbers over time for muscle mimicking material by itself and for the same material in contact with prostate and fat mimicking material.

The scanner determined that T1 changed significantly over the same time frame for tissue-mimicking prostate and tissue-mimicking muscle when they were placed in direct contact with each other and initially had the same concentration of $Cu^{++}$ and EDTA (see FIGS. 3 and 4). This may be ascribed to the lack of equilibrium in the $Cu^{++}$/EDTA concentrations between the two tissue-mimicking materials. T1 for tissue-mimicking prostate steadily declined and increased for tissue-mimicking muscle relative to the controls. An increase in $Cu^{++}$/EDTA tends to decrease the T1. The changes in T1 seen in the tissue-mimicking prostate and tissue-mimicking muscle were explained by the diffusion of $Cu^{++}$/EDTA from the tissue-mimicking muscle side to the tissue-mimicking prostate side causing a lowering of the T1 in tissue-mimicking prostate and consequently a increase in T1 for tissue-mimicking muscle. To lower the concentration of $Cu^{++}$/EDTA in tissue-mimicking muscle, long term stability phantoms were made with 60%, 70%, and 80% of the $Cu^{++}$/EDTA concentration as compared with the original tissue-mimicking muscle sample. From FIGS. 6–9 it can be seen that the tissue-mimicking muscle sample containing 60% $Cu^{++}$/EDTA compared to tissue-mimicking prostate is the preferred material for mimicking skeletal muscle in an anthropomorphic phantom where tissue-mimicking muscle are in direct contact. FIG. 7 shows the time dependence of T1s for muscle mimicking material in two environments: (1) isolated from other tissue-mimicking material with $Cu^{++}$ and EDTA concentrations at 60% of those in reference prostate-mimicking material; and (2) in direct contact with reference prostate-mimicking material with the muscle-mimicking material initially having $Cu^{++}$ and EDTA concentrations at 60% of those in reference prostate-mimicking material.

Figure 24:
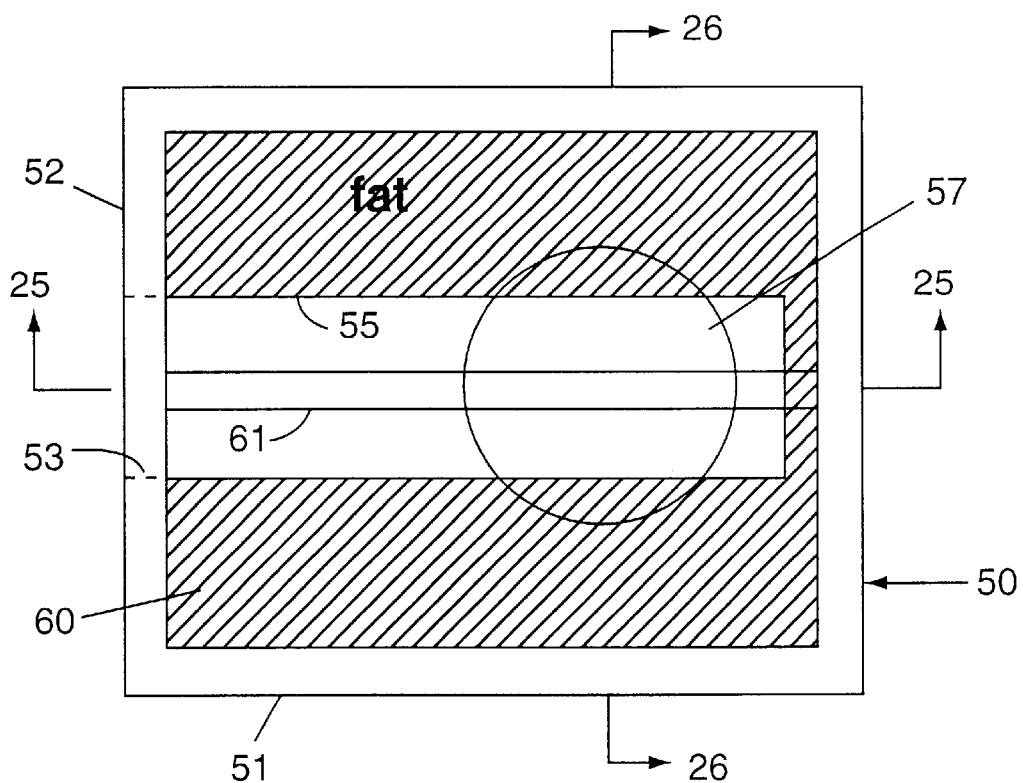
FIG. 24 is a view of an anthropomorphic prostate phantom illustrating the position of various components therein.
Figure 26:
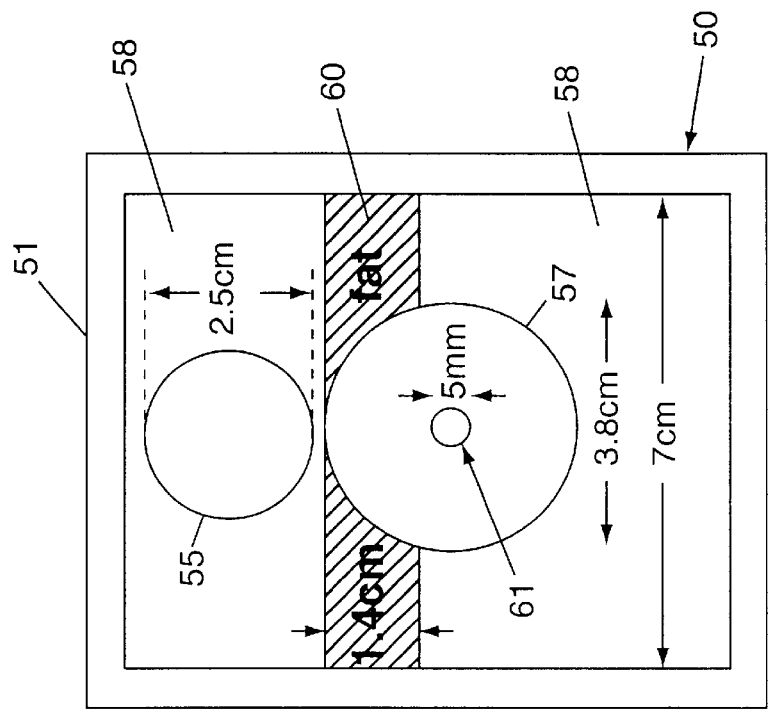
FIG. 26 is a cross-sectional view of the phantom of FIG. 24 taken generally along the lines 26—26 of FIG. 24.
Figure 25:
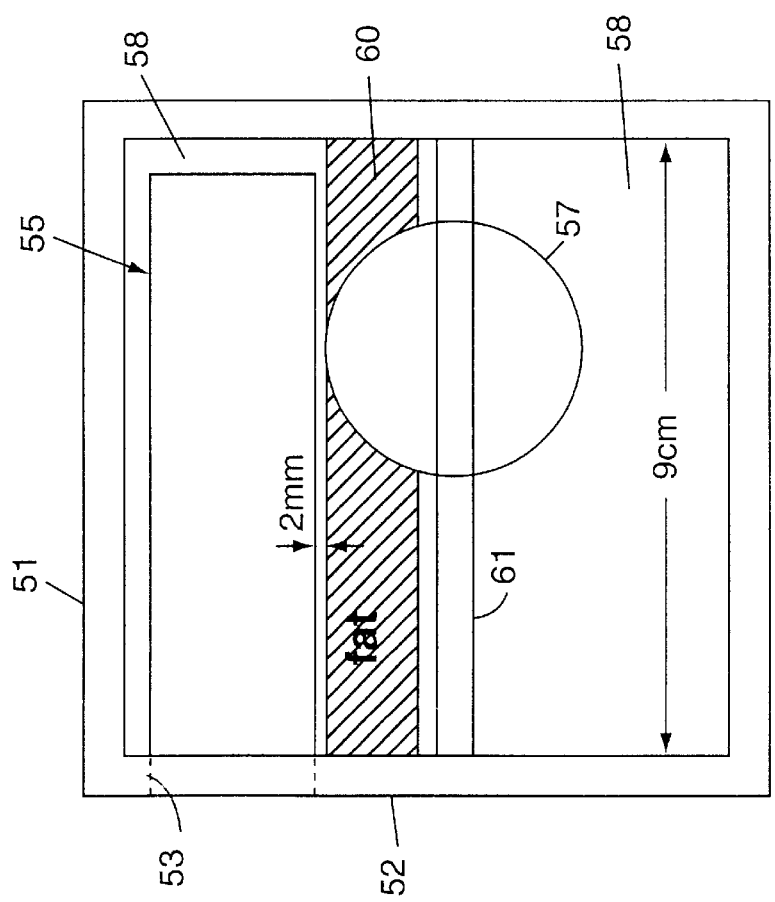
FIG. 25 is a cross-sectional view of the phantom of FIG. 24 taken generally along the lines 25—25 of FIG. 24.

Phantoms in accordance with the present invention can be formed as anthropomorphic phantoms which simulate complex body structures in which multiple types of tissues are in contact with one another. A particular example of an anthropomorphic phantom simulating the prostate and surrounding tissue is shown generally at 50 in the view of FIGS. 24–26. The phantom 50 has a generally rectangular container 51 formed of rigid walls of, e.g., 6.3 mm thick acrylic plastic. One wall 52 of the container has a round opening 53 therein to which is secured a closed cylinder 55 of, e.g., 0.7 mm thick polymethyl pentene. A sphere 57 of tissue-mimicking material is embedded within surrounding tissue-mimicking material 58 which simulates muscle/fascia and in contact with a slab of tissue-mimicking material 60 which simulates fat. The tissue-mimicking material 58 simulating muscle also surrounds the open cylinder 55. A thin cylinder of tissue-mimicking material 61 extends through the muscle simulating material 58 and through the center of the prostate simulating sphere 57. In this arrangement of structures, the sphere 57 simulates the prostate gland in contact with muscle 58 and fat 60, adjacent to the closed cylinder 55 simulating the rectum, with the material simulating the prostate 57, of the muscle 58, and the fat 60 formed, e.g., as described above. The tissue-mimicking material 61 simulating the urethra may be formed of the same material comprising the prostate simulating section 57 with a higher concentration of (e.g., 45–53 μm diameter) glass beads, four times the concentration in the material 57.

The phantom 50 may be used to compare images obtained with various imaging equipment, e.g., ultrasound scanners, MRI imagers and CT scanners, allowing a standardized comparison of the images obtained with each modality. Ultrasound scans may be taken through the walls of the closed cylinder 55 to simulate ultrasound images of the prostate from the rectum. When the phantom is not in use, an appropriate solution is preferably maintained in the cylinder 55 to inhibit desiccation of the gel material in contact with the walls of the cylinder.

The glass beads that are added to the tissue-mimicking muscle material are extremely small, with a mean diameter of about 18 μm. These beads raise the ultrasound attenuation coefficient of the tissue-mimicking muscle and the backscatter coefficient. Larger beads (45–53 μm diameter range) may be added in a much smaller concentration to the tissue-mimicking prostate material with little effect on the tissue-mimicking prostate attenuation coefficient while raising the backscatter coefficient to a range such that the contrast between the tissue-mimicking prostate material and tissue-mimicking muscle material simulates that in a human prostate region on ultrasound images. In accordance with the invention, the addition of beads with various different diameter distributions allows adjustment of attenuation coefficients and backscatter coefficients to clinically representative values.

It is understood that the invention is not confined to the particular embodiments set forth herein, but embraces all such forms thereof as come within the scope of the following claims.

What is claimed is:

1. Multi-imaging modality tissue-mimicking material for phantoms for use with at least ultrasound and MRI comprising:
   an aqueous mixture of large organic water soluble molecules, a copper salt, a chelating agent for binding the copper ions in the salt, a gel-forming material, and beads intermixed therewith to provide a selected ultrasound attenuation coefficient, the beads treated to have a low effect on the MRI T1 and T2 properties of the tissue-mimicking material.

2. The tissue-mimicking material of claim 1 wherein the gel-forming agent is agarose.

3. The tissue-mimicking material of claim 1 wherein the copper salt is $CuCl_2$.

4. The tissue-mimicking material of claim 1 wherein the large organic water soluble molecules are derived from condensed milk.

5. The tissue-mimicking material of claim 1 further including n-propyl alcohol intermixed therewith.

6. The tissue-mimicking material of claim 1 wherein the chelating agent is EDTA.

7. The tissue-mimicking material of claim 1 further comprising thimerosal intermixed therewith as a preservative.

8. The tissue-mimicking material of claim 1 wherein the beads are selected from glass beads that have been treated by a soak in nitric acid to clean the surface thereof to reduce the effect of the glass beads on MRI T1 and T2 properties.

9. Multi-imaging modality tissue-mimicking material for phantoms for use with at least ultrasound and MRI comprising:
an aqueous mixture of large organic water soluble molecules, $CuCl_2$ salt, EDTA as a chelating agent for binding the copper ions in the salt, and a gel-forming material, and glass beads of two different diameters intermixed therewith to provide a selected ultrasound attenuation coefficient and backscatter coefficient, the glass beads selected to have a low effect on the MRI T1 and T2 properties of the tissue-mimicking material.

10. The tissue-mimicking material of claim 9 wherein the glass beads are selected from glass beads that have been treated by a soak in nitric acid to clean the surface thereof to reduce the effect of the glass beads on MRI T1 and T2 properties.

11. The tissue-mimicking material of claim 9 wherein the first, small diameter glass beads have a mean diameter of about 20 µm or less to influence primarily ultrasound and CT attenuation, and the second, large diameter glass beads have a mean diameter of 30 µm or larger to influence primarily ultrasound backscatter.

12. The tissue-mimicking material of claim 9 wherein the gel-forming agent is agarose.

13. The tissue-mimicking material of claim 9 wherein the large organic water soluble molecules are derived from condensed milk.

14. The tissue-mimicking material of claim 9 further including n-propyl alcohol intermixed therewith.

15. The tissue-mimicking material of claim 9 further comprising thimerosal intermixed therewith as a preservative.

16. An imaging phantom for use with at least ultrasound and MRI comprising:
(a) a phantom container;
(b) a tissue-mimicking material within the container, the tissue-mimicking material comprising at least two distinct sections in contact with each other, the two sections having first, small diameter glass beads intermixed therewith to provide a selected ultrasound attenuation coefficient therein, and wherein one of the sections includes second, larger diameter beads intermixed therewith to provide a selected backscatter coefficient therein.

17. The imaging phantom of claim 16 wherein the tissue-mimicking material in at least two sections in contact with each other includes an aqueous mixture of large organic water soluble molecules, a copper salt, a chelating agent for bonding the copper ions in the salt, and a gel-forming material.

18. The imaging phantom of claim 17 wherein the gel-forming agent is agarose.

19. The imaging phantom of claim 18 wherein the section having larger glass beads therein has a higher dry weight concentration of agarose than the other section.

20. The imaging phantom of claim 17 wherein the copper salt is $CuCl_2$.

21. The imaging phantom of claim 17 wherein the large organic water soluble molecules are derived from condensed milk.

22. The imaging phantom of claim 17 further including n-propyl alcohol intermixed therewith.

23. The imaging phantom of claim 17 wherein the chelating agent is EDTA.

24. The imaging phantom of claim 17 further comprising thimerosal intermixed therewith as a preservative.

25. The imaging phantom of claim 16 wherein the beads are selected from glass beads that have been treated by a soak in nitric acid to clean the surface thereof to reduce the effect of the glass beads on MRI T1 and T2 properties.

26. The imaging phantom of claim 16 further including a section of tissue-mimicking material including vegetable oil to simulate fat tissue.

27. The imaging phantom of claim 16 wherein the first, small diameter beads have a mean diameter of about 20 µm or less to influence primarily ultrasound and CT attenuation, and the second, large diameter beads have a mean diameter of 30 µm or greater to influence primarily ultrasound backscatter.

28. The imaging phantom of claim 16 including a third section comprising a polyurethane mesh with interstices filled with oil.

29. The imaging phantom of claim 28 wherein the oil is vegetable oil.

30. An imaging phantom for use with at least ultrasound and MRI comprising:
(a) a phantom container;
(b) a tissue-mimicking material within the container, the tissue-mimicking material comprising at least three distinct sections in contact with each other, the tissue-mimicking material in a first and second section in contact with each other including an aqueous mixture of large organic water soluble molecules, a copper salt, a chelating agent for bonding the copper ions in the salt, and a gel-forming material, the two sections having first, small diameter beads intermixed therewith to provide a selected ultrasound attenuation coefficient therein, and wherein one of the sections includes second, larger diameter beads intermixed therewith to provide a selected backscatter coefficient therein, the glass beads treated to have a low effect on the MRI T1 and T2 properties.

31. The imaging phantom of claim 30 wherein the gel-forming agent is agarose.

32. The imaging phantom of claim 31 wherein the section having larger beads therein has a higher dry weight concentration of agarose than the other section.

33. The imaging phantom of claim 30 wherein the copper salt is $CuCl_2$.

34. The imaging phantom of claim 30 wherein the large organic water soluble molecules are derived from condensed milk.

35. The imaging phantom of claim 30 further including n-propyl alcohol intermixed therewith.

36. The imaging phantom of claim 30 wherein the chelating agent is EDTA.

37. The imaging phantom of claim 30 further comprising thimerosal intermixed therewith as a preservative.

38. The imaging phantom of claim 30 wherein the beads are selected from glass beads that have been treated by a soak in nitric acid to clean the surface thereof to reduce the effect of the glass beads on MRI T1 and T2 properties.

39. The imaging phantom of claim 30 wherein the oil is vegetable oil.

40. The tissue-mimicking material of claim 30 wherein the first, small diameter beads have a mean diameter of about 20 $\mu$m or less to influence primarily ultrasound and CT attenuation, and the second, large diameter beads have a mean diameter of 30 $\mu$m or larger to influence primarily ultrasound backscatter.

41. The imaging phantom of claim 30 wherein the first section is formed as a sphere to simulate prostate tissue, the third section is formed as a slab in contact with the first section to simulate fat tissue, and the second section is formed to surround the first section and the third section and simulates muscle and connective tissue.

42. The imaging phantom of claim 41 further including a closed ended cylindrical wall with an open interior that extends from a wall of the phantom container into the tissue-mimicking material in the container to simulate a rectum.

43. The imaging phantom of claim 42 further including a thin cylinder of tissue-mimicking material extending through the first section and into the material of the second section to simulate a urethra.

* * * * *